US007329487B2

(12) United States Patent
Lee

(10) Patent No.: US 7,329,487 B2
(45) Date of Patent: *Feb. 12, 2008

(54) LARGE SCALE GENOTYPING OF DISEASES AND A DIAGNOSTIC TEST FOR SPINOCEREBELLAR ATAXIA TYPE 6

(75) Inventor: Cheng-Chi Lee, Houston, TX (US)

(73) Assignee: Research Development Foundation, Carson City, NV (US)

( * ) Notice: Subject to any disclaimer, the term of this patent is extended or adjusted under 35 U.S.C. 154(b) by 303 days.

This patent is subject to a terminal disclaimer.

(21) Appl. No.: 10/435,804

(22) Filed: May 12, 2003

(65) Prior Publication Data

US 2004/0023277 A1 Feb. 5, 2004

Related U.S. Application Data

(60) Continuation of application No. 09/093,273, filed on Jun. 8, 1998, now abandoned, and a division of application No. 08/779,801, filed on Jan. 7, 1997, now Pat. No. 5,853,995.

(51) Int. Cl.
C07H 21/04 (2006.01)
C12Q 1/68 (2006.01)

(52) U.S. Cl. .................. 435/6; 435/91.1; 435/91.2; 536/23.1; 536/24.3

(58) Field of Classification Search .................. 435/6, 435/91.1, 91.2, 91.5; 536/23.1, 24.33, 24.3
See application file for complete search history.

(56) References Cited

U.S. PATENT DOCUMENTS 5,853,995 A * 12/1998 Lee ............................... 435/6
6,303,307 B1 * 10/2001 Lee ............................... 435/6

FOREIGN PATENT DOCUMENTS

WO       WO 95/01437       1/1995

OTHER PUBLICATIONS

Shizuka et al (J. of the Neurological Sciences, vol. 161, pp. 85-87, 1998).*
Yabe et al. (J. of the Neurological Sciences, vol. 156, pp. 89-95, 1998).*
Nagai et al (J. of the Neurological Sciences, vol. 157, pp. 52-59, 1998).*
Ishikawa et al. (Am. J. of Human Genetics, vol. 61, pp. 336-346, 1997).*
Zhuchenko et al. "Autosomal dominant cerebellar ataxia (SCA6) assocaited with small polyglutamine expansions in the alpha 1A voltage-dependent calcium channel." Nature Genetics, vol. 15, pp. 62-69, Jan. 1, 1997.*
Ophoff et al. (Cell, vol. 87, pp. 543-552, Nov. 1, 1996).*
Hummerlich and Lehrach, "Trinucleotide repeat expansion and human disease," Electrophoresis, 16:1698-1704, 1995.
Imbert et al., "Cloning of the gene for spinocerebellar ataxia 2 reveals a locus with high sensitivity to expanded CAG/glutamine repeats," Nature Genet., 14:285-291, 1996.
Kawaguchi et al., "CAG expansions in a novel gene for Machado-Joseph disease at chromosome 14q32.1." Nature Genet., 8:221-228, 1994.
Koide et al., "Unstable expansion of CAG repeat in hereditary dentatorubral-pallidoluysian atropy (DRPLA)," Nature Genet., 6:9-13, 1994.
La Spada, et al., "Androgen receptor gene mutations in X-linked spinal and bulbar muscular atrophy," Nature 352:77-79, 1991.
Orr et al., "Expansion of an unstable trinucleotide CAG repeat in spinocerebellar ataxia type 1," Nature Genet., 4:221-226, 1993.
Pulst et al., "Moderate expansion of a normally biallelic trinucleotide repeat in spinocerebellar ataxia type 2," Nature Genet., 14:269-276, 1996.
The Huntington Disease Collaborative Research Group., "A novel gene containing a trinucleotide repeat that is expanded and unstable on Huntington's disease chromosomes," Cell, 72:971-983, 1993.
Warren, "The expanding world of trinucleotide repeats." Science, 271:1374-1375, 1996.
Margolis, et al. *cDNA Cloning of a Human Homologue of the Caenorhabditis elegans cell fate-determining gene* mab-12: *expression, chromosomal localization and analysis of a highly polymorphic (CAG)n trinucleotide repeat*. Human Molecular Genetics, vol. 5, No 5, pp. 607-616 (1996).
Riggins, et al. *Human Genes Containing Polymorphic Trinucleotide Repeats*. Nature Genetics, vol. 2, pp. 186-191 (1992).
Sanpei, et al., *Identification of the Spinocerebellar Ataxia Type 2 Gene Using a Direct Identification of Repeat Expansion and Cloning Technique,DIRECT*. Nature Genetics, vol. 14, pp. 277-284 (1996).
Chung, et al. *Evidence for a Mechanism Predisposing to Intergenerational CAG Repeat Instability in Spinocerebellar Ataxia Type I*. Nature Genetics, vol. 5, pp. 254-258 (1993).
Riess, et al. *SCA6 is Caused by Moderate CAG Expansion in the α1A-Volatage-Dependent Calcim Channel Gene*. Human Molecular Genetics, vol. 6, No. 8 pp. 1289-1293 (1997).
Matsuyama, et al. *Molecular Features of the CAG Repeats of Spinocerebellar Ataxia 6 (SCA6)*. Human Molecular Genetics, vol. 6, No. 8 pp. 1283-1287 (1997).
Zhuchenko, et al. *Autosomal Dominant Cerebellar Ataxia (SCA6) Associated with Small Polyglutamine Expansions in the α1A-Voltage-Dependent Calcium Channel*. Nature Genetics, vol. 15, pp. 62-69 (1997).
Ishikawa, et al. *Japanese Families with Autosomal Dominant Pure Cerebellar Ataxia Map to Chromosome 19p13.1-p13.2 and Are Strongly Associated with Mild CAG Expansions in the Spinocerebellar Ataxia Type 6 Gene in Chromosome 19p13.1*. American Journal of Human Genetics, vol. 61, pp. 336-346 (1997).

* cited by examiner

Primary Examiner—Jeanine A. Goldberg
(74) Attorney, Agent, or Firm—Fulbright & Jaworski L.L.P.

(57) ABSTRACT

The present invention provides a method of screening individuals at risk for developing diseases caused by trinucleotide repeat sequence instability. Specifically, the present invention is drawn to screening individuals at risk for developing autosomal dominant spinocerebellar ataxia type 6 by determining the length of a CAG trinucleotide repeat in the $\alpha_{1A}$ calcium channel gene of the individual. In addition, there is provided a method of identifying genes which are disease-causing due to trinucleotide repeat sequence instability by large scale genotyping.

25 Claims, 10 Drawing Sheets

```
OCCCBI1   1301  MVIKMIDLGL  VLHQGAYFRD  LWNILDFIVV  SGALVAFAFT  GNSKGKDINT
Human cDNA      ----------  ----------  ----------  ----------  ----------

OCCCBI1   1351  IKSLRVLRVL  RPLKTIKRLP  KLKAVFDCVV  NSLKNVFNIL  IVYMLFMFIF
Human cDNA      ----------  ----------  ----------  ----------  ----------

OCCCBI1   1401  AVVAVQLFKG  KFFHCTDESK  EFEKDCRGKY  LLYEKNEVKA  RDREWKKYEF
Human cDNA      ----------  ----------  ----------  ----------  ----------

OCCCBI1   1451  HYDNVLWALL  TLFTVSTGEG  WPQVLKHSVD  ATFENQGPSP  GYRMEMSIFY
Human cDNA      ----------  ----------  ----------  ----------  ----------

OCCCBI1   1501  VVYFVVFPFF  FVNIFVALII  ITFQEQGDKM  MEEYSLEKNE  RACIDFAISA
Human cDNA      ----------  ----------  ----------  ----------  ----------

OCCCBI1   1551  KPLTRHMPQN  KQSFQYRMWQ  FVVSPPFEYT  IMAMIALNTI  VLMMKFYGAS
Human cDNA      ----------  ----------  ----------  ----------  ----------

OCCCBI1   1601  VAYDNALKVF  NIVFTSLFSL  ECLLKVLAFG  ILNYFRDAWN  IFDFVTVLGS
Human cDNA      ---E---R--  ----------  --V---M---  ----------  ----------

OCCCBI1   1651  ITDILVTEFG  NNFINLSFLR  LFRAARLIKL  LRQGYTIRIL  LWTFVQSFKA
Human cDNA      ----------  ----------  ----------  ----------  ----------

OCCCBI1   1701  LPYVCLLIAM  LFFIYAIIGM  QVFGNIGIDM  EDEDSDEDEF  QITEHNNFRT
Human cDNA      ----------  ----------  ----------  ---------V  ----------

OCCCBI1   1751  FFQALMLLFR  SATGEAWHNI  MLSCLSGKPC  DKNSGILTPE  CGNEFAYFYF
Human cDNA      ----------  ----------  ----------  --------R-  ----------
```

Fig. 2A

```
OCCCBI1 1801  VSFIFLCSFL MLNLFVAVIM DNFEYLTRDS SILGPHHLDE YVRVWAEYDP
Human cDNA    ---------- ---------- ---------- ---------- ---------- variation 1
OCCCBI1 1851  AAWGRMLYRD MYAMLRHMPP PLGLGKNCPA RVAYKRLLRM DLPVADDNTV
Human cDNA    -----P-L-- ---Q------ -------S-- -----K---- ----------
              C--IH-K--- ---SL--VIS ---------- -----K--H- ----------

OCCCBI1 1901  HFNSTLMALI RTALDIKIAK GGADKQQMDA ELRKEMMAIW PNLSQKTLDL
Human cDNA    ---------- ---------- ---------- ---------- ----------

OCCCBI1 1951  LVTPHKSTDL TVGKIYAAMM IMEYYRQSKA KKLQAMREEQ NRTPLMFQRM
Human cDNA    ---------- ---G-A---- ---------- ---------- D---------

OCCCBI1 2001  EPP.PD.EGG AGQNALPSTQ LDPAGGLMAH EDGLKDSPSW VTQRAQEMFQ
Human cDNA    ---S-TQ--- P--------- ---------- -S----E--- ----------

OCCCBI1 2051  KTGTWSPERA PPADMADSQP KPQSVEMREM SQDGYSDSEH CLPMEGQARA
Human cDNA    ------QG-- --T--PN--- NS-------- GR-------- Y------G-- variation 2
OCCCBI1 2101  ASMPRLPAEN QRRRGRPRGS DLSTICDTSP MKRSASVLGP KASRRLLDDYS
Human cDNA    ---------- ---------- ---N----S- ---------- ---------·-
                                    N-|-    |

OCCCBI1 2151  LERVPPEENQ RHHPRRRERA HRTSERSLGR YTDVDTGLGT DLSMTTQSGD
Human cDNA    ---------- ---Q--D-S- ---A------ ---------- ----------
```

Fig. 2B

```
                                                                    variation_3
OCCCBI1 2201  LPSREREQER GRPKDRKHRP HHHHHHHHP GPAAADKERY GPQDRPDHGH
Human cDNA    ---------- -----D---- --------Q --H-P-PP.- -A.-E-----.
                                                        R_FLCFFPFFL_PCLKTVGLGL OCCCBI1 2251  GRARARDQRW SRSPSEGREH TTHRQGSSSV SGSPVPSTSG TSTPQRGRRQ
Human cDNA    ---------- ----T----- --MA------ ---------- ----R-----
              |_____|
                         *          /\
                                    GGCAG insertion OCCCBI1 2301  LPQTPCTPRP LVSYSPVVRK VGGVGPPQQQ Q........AV ARPGRAAPGG
Human cDNA    ---------S ----H----- ---A--S--- -QQQQQQ--- --------TS- OCCCBI1 2351  PRRYPGPAAE PPPA.....G GHGAGRSPAL ERRGPGAARD ESPRACRHGG
Human cDNA    ---------- -LAGDRPPT- ---SS----RM ---V--P--S ----------

OCCCBI1 2401  GGGARWPASG PHAHPHSHTH AHAHTHGYYR SSDYDEPEGP GRGSGGGLGD
Human cDNA    ........-- --VSEGPP.. -GPR-.---- -G-----AD- ------EEA- OCCCBI1 2451  DEEVAAGPYA APPGPAS... RSPRTPRAAG PACASPARHG RRVPNGYYPV
Human cDNA    MAGAYDA-PP VRHASSGATG -S-------- ---S------ ---L------A OCCCBI1 2501  HGLARPRGPG SRKSLHEVYS ESDEDWC*
Human cDNA    ---------- ---G----P- ---D----
```

Fig. 2C

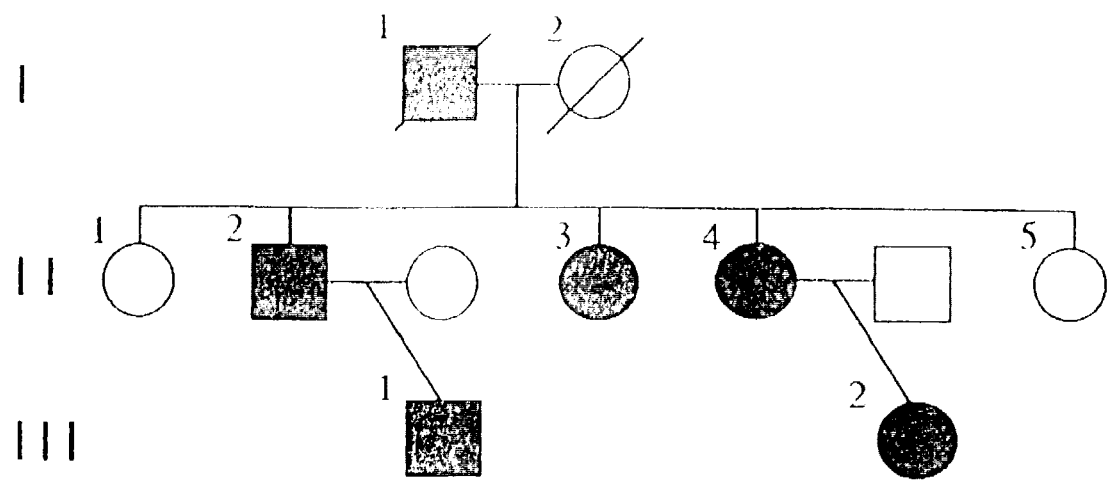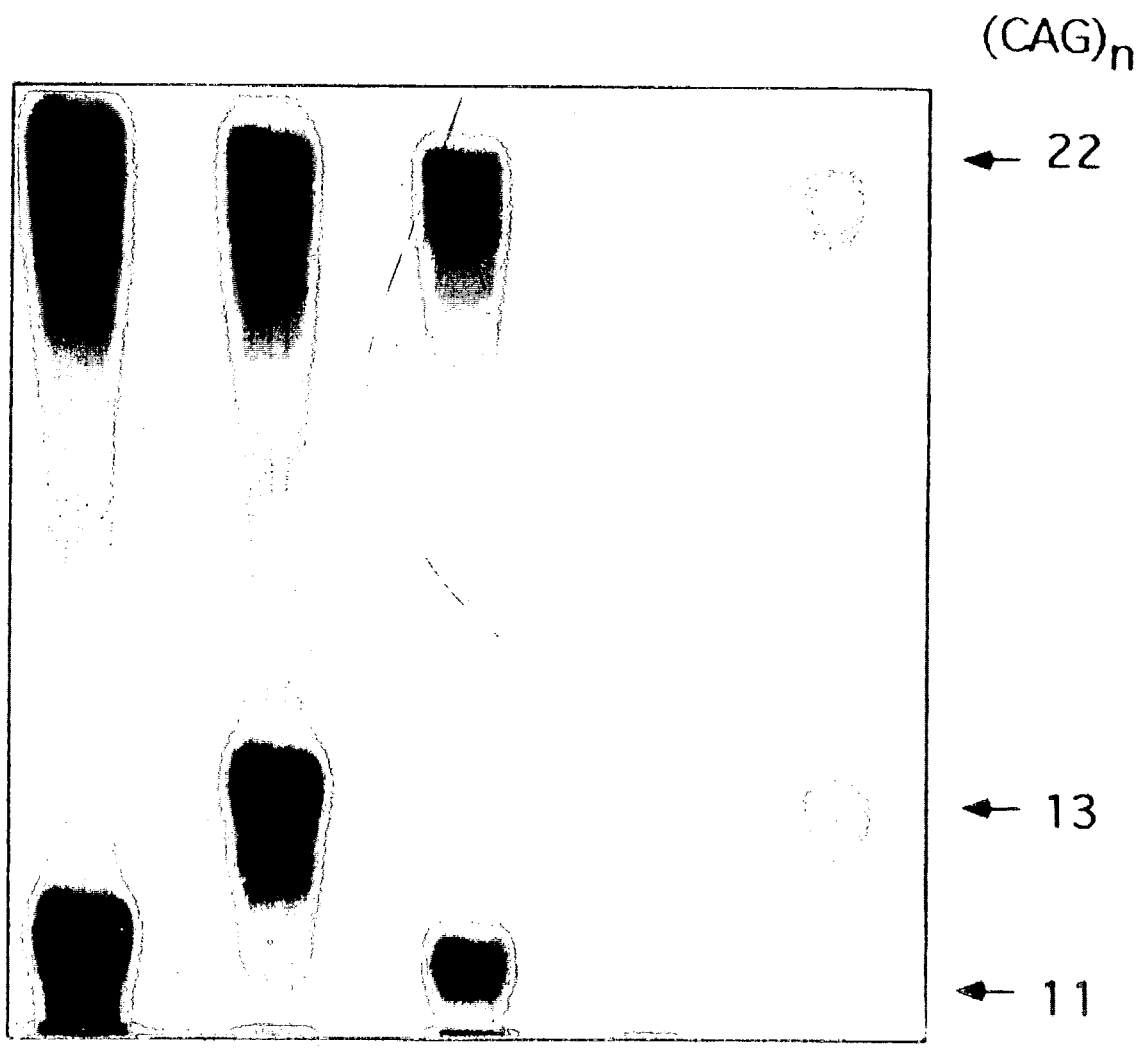
Fig. 4B

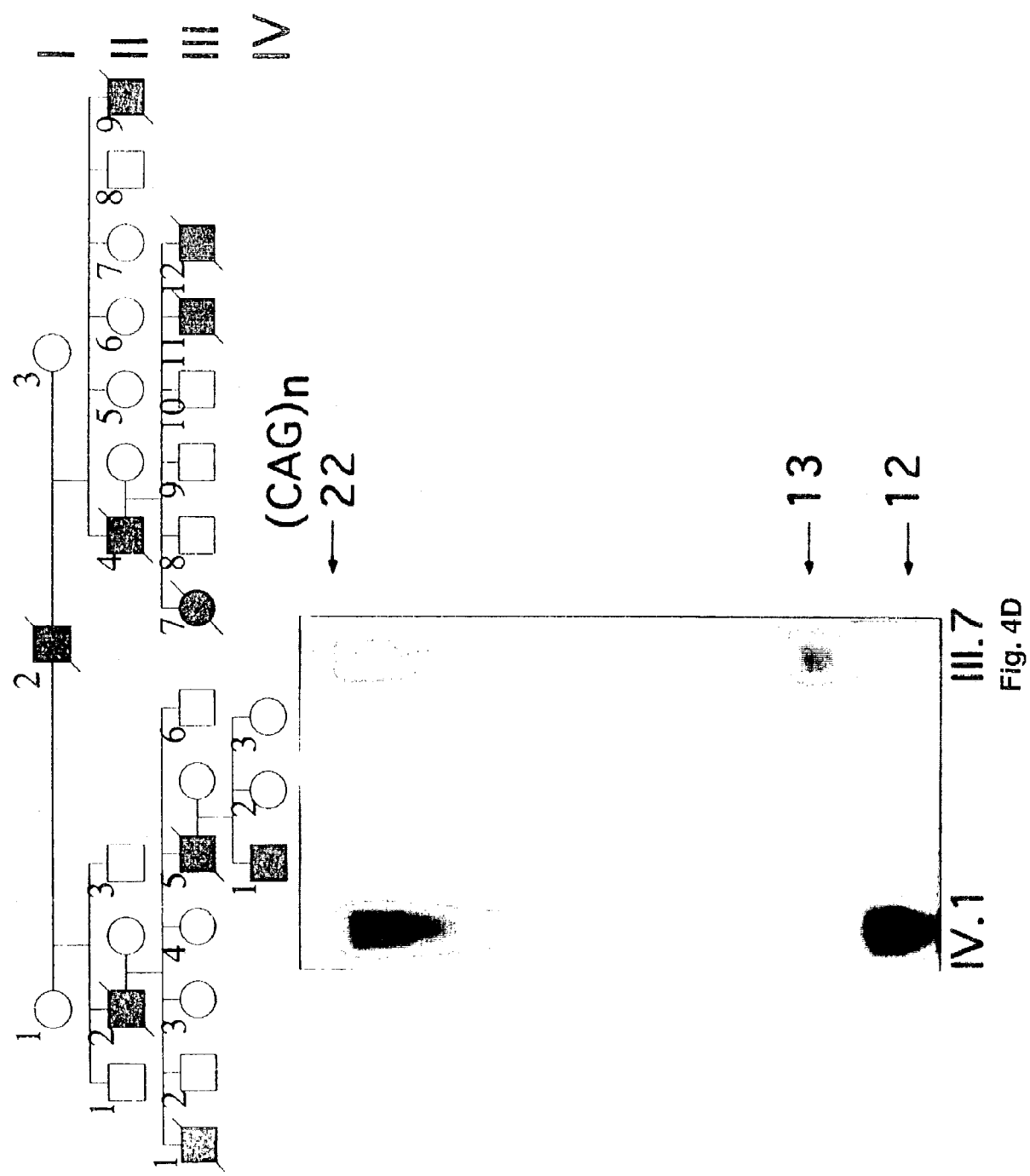

SEQUENCE LISTING

```
<160> NUMBER OF SEQ ID NOS: 5

<210> SEQ ID NO 1
<211> LENGTH: 25
<212> TYPE: DNA
<213> ORGANISM: artificial sequence
<220> FEATURE:
<221> NAME/KEY: primer
<223> OTHER INFORMATION: Nucleotide sequence of S-5-F1 forward primer

<400> SEQUENCE: 1
cacgtgtcct attcccctgt gatcc                                          25

<210> SEQ ID NO 2
<211> LENGTH: 25
<212> TYPE: DNA
<213> ORGANISM: artificial sequence
<220> FEATURE:
<221> NAME/KEY: primer
```

<223> OTHER INFORMATION: Nucleotide sequence of S-5-R1 reverse primer

<400> SEQUENCE: 2
tgggtacctc cgagggccgc tggtg                                      25

<210> SEQ ID NO 3
<211> LENGTH: 3632
<212> TYPE: DNA
<213> ORGANISM: artificial sequence
<220> FEATURE:
<223> OTHER INFORMATION: Nucleotide sequence of BI-1 isoform in
      combination with the GGCAG insertion

<400> SEQUENCE: 3

```
gaattcttcc actcgacttc atagtggtca gtggggccct ggtagccttt gccttcactg    60
gcaatagcaa aggaaaagac atcaacacga ttaaatccct ccgagtcctc cgggtgctac   120
gacctcttaa aaccatcaag cggctgccaa agctcaaggc tgtgtttgac tgtgtggtga   180
actcacttaa aaacgtcttc aacatcctca tcgtctacat gctattcatg ttcatcttcg   240
ccgtggtggc tgtgcagctc ttcaagggga aattcttcca ctgcactgac gagtccaaag   300
agtttgagaa agattgtcga ggcaaatacc tcctctacga aagaatgag gtgaaggcgc   360
gagaccggga gtggaagaag tatgaattcc attacgacaa tgtgctgtgg gctctgctga   420
ccctcttcac cgtgtccacg ggagaaggct ggccacaggt cctcaagcat tcggtggacg   480
ccaccttgta gaaccagggc cccagccccg ggtaccgcat ggagatgtcc attttctacg   540
tcgtctactt tgtggtgttc cccttcttct ttgtcaatat ctttgtggcc ttgatcatca   600
tcaccttcca ggagcaaggg acaagatga tggaggaata cagcctggag aaaaatgaga   660
gggcctgcat tgatttcgcc atcagcgcca agccgctgac ccgacacatg ccgcagaaca   720
agcagagctt ccagtaccgc atgtggcagt cgtggtgtc tccgcctttc gagtacacga   780
tcatggccat gatcgccctc aacaccatcg tgcttatgat gaagttctat ggggcttctg   840
ttgcttatga aaatgccctg cgggtgttca acatcgtctt cacctccctc ttctctctgg   900
aatgtgtgct gaaagtcatg gcttttggga ttctgaatta tttccgcgat gcctggaaca   960
tcttcgactt tgtgactgtt ctgggcagca tcaccgatat cctcgtgact gagtttggga  1020
ataacttcat caacctgagc tttctccgcc tcttccgagc tgcccggctc atcaaactc  1080
tccgtcaggg ttacaccatc cgcattcttc tctggacctt tgtgcagtcc ttcaaggccc  1140
tgccttatgt ctgtctgctg atcgccatgc tcttcttcat ctatgccatc attgggatgc  1200
aggtgtttgg taacattggc atcgacgtgg aggacgagga cagtgatgaa gatgagttcc  1260
aaatcactga gcacaataac ttccggacct tcttccaggc cctcatgctt ctcttccgga  1320
gtgccaccgg ggaagcttgg cacaacatca tgctttcctg cctcagcggg aaaccgtgtg  1380
ataagaactc tggcatcctg actcgagagt gtggcaatga atttgcttat ttttactttg  1440
tttccttcat cttcctctgc tcgtttctga tgctgaatct ctttgtcgcc gtcatcatgg  1500
acaactttga gtacctcacc cgagactcct ccatcctggg cccccaccac ctggatgagt  1560
acgtgcgtgt ctgggccgag tatgaccccg cagcttgggg ccgcatgcct tacctggaca  1620
tgtatcagat gctgagacac atgtctccgc ccctgggtct ggggaagaag tgtccggcca  1680
gagtggctta caagcggctt ctgcggatgg acctgccccg tcgcagatgac aacaccgtcc  1740
acttcaattc caccctcatg gctctgatcc gcacagccct ggacatcaag attgccaagg  1800
gaggagccga caacagcag atggacgctg agctgcggaa ggagatgatg gcgatttggc  1860
```

-continued

```
ccaatctgtc ccagaagacg ctagacctgc tggtcacacc tcacaagtcc acggacctca   1920
ccgtggggaa gatctacgca gccatgatga tcatggagta ctaccggcag agcaaggcca   1980
agaagctgca ggccatgcgc gaggagcagg accggacacc cctcatgttc agcgcatgg    2040
agcccccgtc cccaacgcag gaaggggggac ctggccagaa cgccctcccc tccacccagc  2100
tggacccagg aggagccctg atggctcacg aaagcggcct caaggagagc ccgtcctggg   2160
tgacccagcg tgcccaggag atgttccaga gacgggcac atggagtccg gaacaaggcc    2220
cccctaccga catgcccaac agccagccta actctcagtc cgtggagatg cgagagatgg   2280
gcagagatgg ctactccgac agcgagcact acctcccccat ggaaggccag ggccgggctg  2340
cctccatgcc ccgcctccct gcagagaacc agaggagaag gggccggcca cgtgggaata   2400
acctcagtac catctcagac accagcccca tgaagcgttc agcctccgtg ctgggcccca   2460
aggcccgacg cctggacgat tactcgctgg agcgggtccc gcccgaggag aaccagcggc   2520
accaccagcg gcgccgcgac cgcagccacc gcgcctctga gcgctccctg ggccgctaca   2580
ccgatgtgga cacaggcttg ggacagacc tgagcatgac cacccaatcc ggggacctgc    2640
cgtcgaagga gcgggaccag gagcggggcc ggcccaagga tcggaagcat cgacagcacc   2700
accaccacca ccaccaccac caccatcccc cgccccccga caaggaccgc tatgcccagg   2760
aacggccgga ccacgccgg gcacgggctc ggaccagcg ctggtcccgc tcgcccagcg     2820
agggccgaga gcacatggcg caccggcagg gcagtagttc cgtaagtgga gcccagccc    2880
cctcaacatc tggtaccagc actccgcggc ggggccgccg ccagctcccc cagacccct    2940
ccacccccg gccacacgtg tcctattccc ctgtgatccg taaggccggc ggctcggggc    3000
ccccgcagca gcagcagcag cagcagcagc agcagcagca ggcggtggcc aggccgggcc   3060
gggcggccac cagcggccct cggaggtacc caggccccac ggccgagcct ctggccggag   3120
atcggccgcc cacgggggggc cacagcagcg gccgctcgcc caggatggag aggcgggtcc   3180
caggcccggc ccggagcgag tccccaggg cctgtcgaca cggcggggcc cggtggccgg     3240
catctggccc gcacgtgtcc gaggggcccc cgggtcccg gcaccatggc tactaccggg    3300
gctccgacta cgacgaggcc gatggcccgg gcagcggggg cggcgaggag gccatggccg   3360
gggcctacga cgcgccaccc cccgtacgac acgcgtcctc gggcgccacc gggcgctcgc    3420
ccaggactcc ccgggcctcg ggcccggcct gcgcctcgcc ttctcggcac ggccggcgac    3480
tccccaacgg ctactacccg cgcacggac tggccaggcc ccgcgggccg ggctccagga    3540
agggcctgca cgaaccctac agcgagagtg acgatgattg gtgctaagcc cgggcgaggg   3600
aattccttttt tttttttttt tttttttttt tt                                3632
```

<210> SEQ ID NO 4
<211> LENGTH: 3632
<212> TYPE: DNA
<213> ORGANISM: artificial sequence
<220> FEATURE:
<223> OTHER INFORMATION: Nucleotide sequence of BI-1(V1) isoform in
      combination with the GGCAG insertion

<400> SEQUENCE: 4

```
gaattcttcc actcgacttc atagtggtca gtggggccct ggtagccttt gccttcactg     60
gcaatagcaa aggaaaagac atcaacacga ttaaatccct ccgagtcctc cgggtgctac   120
gacctcttaa aaccatcaag cggctgccaa agctcaaggc tgtgtttgac tgtgtggtga   180
actcacttaa aaacgtcttc aacatcctca tcgtctacat gctattcatg ttcatcttcg   240
```

-continued

| | |
|---|---|
| ccgtggtggc tgtgcagctc ttcaaggga aattcttcca ctgcactgac gagtccaaag | 300 |
| agtttgagaa agattgtcga ggcaaatacc tcctctacga gaagaatgag gtgaaggcgc | 360 |
| gagaccggga gtggaagaag tatgaattcc attacgacaa tgtgctgtgg gctctgctga | 420 |
| ccctcttcac cgtgtccacg ggagaaggct ggccacaggt cctcaagcat tcggtggacg | 480 |
| ccacctttga gaaccagggc cccagccccg ggtaccgcat ggagatgtcc attttctacg | 540 |
| tcgtctactt tgtggtgttc cccttcttct ttgtcaatat ctttgtggcc ttgatcatca | 600 |
| tcaccttcca ggagcaaggg gacaagatga tggaggaata cagcctggag aaaaatgaga | 660 |
| gggcctgcat tgatttcgcc atcagcgcca agccgctgac ccgacacatg ccgcagaaca | 720 |
| agcagagctt ccagtaccgc atgtggcagt tcgtggtgtc tccgcctttc gagtacacga | 780 |
| tcatggccat gatcgccctc aacaccatcg tgcttatgat gaagttctat ggggcttctg | 840 |
| ttgcttatga aaatgccctg cgggtgttca acatcgtctt cacctccctc ttctctctgg | 900 |
| aatgtgtgct gaaagtcatg gcttttggga ttctgaatta tttccgcgat gcctggaaca | 960 |
| tcttcgactt tgtgactgtt ctgggcagca tcaccgatat cctcgtgact gagtttggga | 1020 |
| ataacttcat caacctgagc tttctccgcc tcttccgagc tgcccggctc atcaaacttc | 1080 |
| tccgtcaggg ttacaccatc cgcattcttc tctggacctt tgtgcagtcc ttcaaggccc | 1140 |
| tgccttatgt ctgtctgctg atcgccatgc tcttcttcat ctatgccatc attgggatgc | 1200 |
| aggtgtttgg taacattggc atcgacgtgg aggacgagga cagtgatgaa gatgagttcc | 1260 |
| aaatcactga gcacaataac ttccggacct tcttccaggc cctcatgctt ctcttccgga | 1320 |
| gtgccaccgg ggaagcttgg cacaacatca tgctttcctg cctcagcggg aaaccgtgtg | 1380 |
| ataagaactc tggcatcctg actcgagagt gtggcaatga atttgcttat ttttactttg | 1440 |
| tttccttcat cttcctctgc tcgtttctga tgctgaatct ctttgtcgcc gtcatcatgg | 1500 |
| acaactttga gtacctcacc cgagactcct ccatcctggg cccccaccac ctggatgagt | 1560 |
| acgtgcgtgt ctgggccgag tatgacccccg cagcttgcgg tcggattcat tataaggata | 1620 |
| tgtacagttt attacgagta atatctcccc ctctcggctt aggcaagaaa tgtcctcata | 1680 |
| gggttgcttg caagcggctt ctgcggatgg acctgcccgt cgcagatgac aacaccgtcc | 1740 |
| acttcaattc caccctcatg gctctgatcc gcacagccct ggacatcaag attgccaagg | 1800 |
| gaggagccga caaacagcag atggacgctg agctgcggaa ggagatgatg gcgatttggc | 1860 |
| ccaatctgtc ccagaagacg ctagacctgc tggtcacacc tcacaagtcc acggacctca | 1920 |
| ccgtggggaa gatctacgca gccatgatga tcatggagta ctaccggcag agcaaggcca | 1980 |
| agaagctgca ggccatgcgc gaggagcagg accggacacc cctcatgttc cagcgcatgg | 2040 |
| agcccccgtc cccaacgcag gaaggggac ctggccagaa cgccctcccc tccacccagc | 2100 |
| tggacccagg aggagccctg atggctcacg aaagcggcct caaggagagc ccgtcctggg | 2160 |
| tgacccagcg tgcccaggag atgttccaga gacgggcac atggagtccg gaacaaggcc | 2220 |
| cccctaccga catgcccaac agccagccta actctcagtc cgtggagatg cgagagatgg | 2280 |
| gcagagatgg ctactccgac agcgagcact acctccccat ggaaggccag ggccgggctg | 2340 |
| cctccatgcc ccgcctccct gcagagaacc agaggagaag gggccggcca cgtgggaata | 2400 |
| acctcagtac catctcagac accagcccca tgaagcgttc agcctccgtg ctgggccccca | 2460 |
| aggcccgacg cctggacgat tactcgctgg agcgggtccc gcccgaggag aaccagcggc | 2520 |
| accaccagcg gcgccgcgac cgcagccacc gcgcctctga cgctccctgg gccgctacaa | 2580 |
| ccgatgtgga cacaggcttg ggacagacc tgagcatgac cacccaatcc ggggacctgc | 2640 |

```
cgtcgaagga gcgggaccag gagcggggcc ggcccaagga tcggaagcat cgacagcacc    2700
accaccacca ccaccaccac caccatcccc cgccccccga caaggaccgc tatgcccagg    2760
aacggccgga ccacggccgg gcacgggctc gggaccagcg ctggtcccgc tcgcccagcg    2820
agggccgaga gcacatggcg caccggcagg gcagtagttc cgtaagtgga agcccagccc    2880
cctcaacatc tggtaccagc actccgcggc ggggccgccg ccagctcccc cagacccccc    2940 ccacccccg gccacacgtg tcctattccc ctgtgatccg taaggccggc ggctcggggc    3000
ccccgcagca gcagcagcag cagcagcagc agcagcaggc agcggtggcc aggccgggcc    3060
gggcggccac cagcggccct cggaggtacc caggcccac ggccgagcct ctggccggag    3120
atcggccgcc cacgggggc cacagcagcg gccgctcgcc caggatggag aggcgggtcc    3180
caggcccggc ccggagcgag tcccccaggg cctgtcgaca cggcggggcc cggtggccgg    3240
catctggccc gcacgtgtcc gaggggcccc cgggtcccg gcaccatggc tactaccggg    3300
gctccgacta cgacgaggcc gatggcccgg gcagcggggg cggcgaggag gccatggccg    3360
gggcctacga cgcgccaccc cccgtacgac acgcgtcctc gggcgccacc gggcgctcgc    3420
ccaggactcc ccgggcctcg ggcccggcct gcgcctcgcc ttctcggcac ggccggcgac    3480
tccccaacgg ctactacccg gcgcacggac tggccaggcc ccgcgggccg ggctccagga    3540
agggcctgca cgaaccctac agcgagagtg acgatgattg gtgctaagcc cgggcgaggg    3600
aattcctttt tttttttttt tttttttttt tt                                 3632
```

<210> SEQ ID NO 5
<211> LENGTH: 3596
<212> TYPE: DNA
<213> ORGANISM: artificial sequence
<220> FEATURE:
<223> OTHER INFORMATION: Nucleotide sequence of the BI-1(V2)-GGCAG
      splice variant including 36 nucleotide deletion and a
      variant with a truncated 3' region BI-1-(V2,V3)

<400> SEQUENCE: 5

```
gaattcttcc actcgacttc atagtggtca gtggggccct ggtagccttt gccttcactg      60
gcaatagcaa aggaaaagac atcaacacga ttaaatccct ccgagtcctc cgggtgctac    120
gacctcttaa aaccatcaag cggctgccaa agctcaaggc tgtgtttgac tgtgtggtga    180
actcacttaa aaacgtcttc aacatcctca tcgtctacat gctattcatg ttcatcttcg    240
ccgtggtggc tgtgcagctc ttcaagggga aattcttcca ctgcactgac gagtccaaag    300
agtttgagaa agattgtcga ggcaaatacc tcctctacga aagaatgag gtgaaggcgc    360 gagaccggga gtgaagaag tatgaattcc attacgacaa tgtgctgtgg gctctgctga    420 cctcttcac cgtgtccacg ggagaaggct ggccacaggt cctcaagcat tcggtggacg    480
ccacctttga gaaccagggc cccagccccg gtaccgcat ggagatgtcc attttctacg    540
tcgtctactt tgtggtgttc cccttcttct ttgtcaatat ctttgtggcc ttgatcatca    600
tcaccttcca ggagcaaggg gacaagatga tggaggaata cagcctggag aaaaatgaga    660
gggcctgcat tgatttcgcc atcagcgcca agccgctgac ccgacacatg ccgcagaaca    720
agcagagctt ccagtaccgc atgtggcagt tcgtggtgtc tccgcctttc gagtacacga    780
tcatggccat gatcgccctc aacaccatcg tgcttatgat gaagttctat ggggcttctg    840
ttgcttatga aaatgccctg cgggtgttca acatcgtctt cacctccctc ttctctctgg    900
aatgtgtgct gaaagtcatg gctttgga ttctgaatta tttccgcgat gcctggaaca    960
```

-continued

```
tcttcgactt tgtgactgtt ctgggcagca tcaccgatat cctcgtgact gagtttggga    1020
ataacttcat caacctgagc tttctccgcc tcttccgagc tgcccggctc atcaaacttc    1080
tccgtcaggg ttacaccatc cgcattcttc tctggacctt tgtgcagtcc ttcaaggccc    1140
tgccttatgt ctgtctgctg atcgccatgc tcttcttcat ctatgccatc attgggatgc    1200
aggtgtttgg taacattggc atcgacgtgg aggacgagga cagtgatgaa gatgagttcc    1260
aaatcactga gcacaataac ttccggacct tcttccaggc cctcatgctt ctcttccgga    1320
gtgccaccgg ggaagcttgg cacaacatca tgctttcctg cctcagcggg aaaccgtgtg    1380
ataagaactc tggcatcctg actcgagagt gtggcaatga atttgcttat ttttactttg    1440
tttccttcat cttcctctgc tcgtttctga tgctgaatct ctttgtcgcc gtcatcatgg    1500
acaactttga gtacctcacc cgagactcct ccatcctggg cccccaccac ctggatgagt    1560
acgtgcgtgt ctgggccgag tatgaccccg cagcttgggg ccgcatgcct tacctggaca    1620
tgtatcagat gctgagacac atgtctccgc ccctgggtct ggggaagaag tgtccggcca    1680
gagtggctta caagcggctt ctgcggatgg acctgcccgt cgcagatgac aacaccgtcc    1740
acttcaattc caccctcatg gctctgatcc gcacagccct ggacatcaag attgccaagg    1800
gaggagccga caaacagcag atggacgctg agctgcggaa ggagatgatg gcgatttggc    1860
ccaatctgtc ccagaagacg ctagacctgc tggtcacacc tcacaagtcc acggacctca    1920
ccgtggggaa gatctacgca gccatgatga tcatggagta ctaccggcag agcaaggcca    1980
agaagctgca ggccatgcgc gaggagcagg accggacacc cctcatgttc cagcgcatgg    2040 agccccgtc cccaacgcag gaaggggac ctggccagaa cgccctcccc tccacccagc    2100
tggacccagg aggagccctg atggctcacg aaagcggcct caaggagagc ccgtcctggg    2160
tgacccagcg tgcccaggag atgttccaga gacgggcac atggagtccg gaacaaggcc    2220
cccctaccga catgcccaac agccagccta actctcagtc cgtggagatg cgagagatgg    2280
gcagagatgg ctactccgac agcgagcact acctccccat ggaaggccag ggccgggctg    2340
cctccatgcc ccgcctccct gcagagaacc agaccatctc agacaccagc cccatgaagc    2400
gttcagcctc cgtgctgggc cccaaggccc gacgcctgga cgattactcg ctggagcggg    2460
tcccgcccga ggagaaccag cggcaccacc agcggcgccg cgaccgcagc caccgcgcct    2520
ctgagcgctc cctgggccgc tacaccgatg tggacacagg cttggggaca gacctgagca    2580
tgaccaccca atccggggac ctgccgtcga aggagcggga ccaggagcgg ggccggccca    2640
aggatcggaa gcatcgacag caccaccacc accaccacca ccaccaccat cccccgcccc    2700
ccgacaagga ccgctatgcc caggaacggc cggaccacgg ccgggcacgg gctcgggacc    2760
agcgctggtc ccgtcgcccc agcgagggcc gagagcacat ggcgcaccgg cagggcagta    2820
gttccgtaag tggaagccca gcccctcaa catctggtac cagcactccg cggcggggcc    2880
gccgccagct cccccagacc ccctccaccc cccggccaca cgtgtcctat tcccctgtga    2940
tccgtaaggc cggcggctcg ggccccccgc agcagcagca gcagcagcag cagcagcagc    3000
agcaggcggt ggccaggccg ggccgggcgg ccaccagcgg ccctcggagg tacccaggcc    3060
ccacggccga gcctctggcc ggagatcggc cgcccacggg gggccacagc agcggccgct    3120
cgcccaggat ggagaggcgg gtcccaggcc cggcccggag cgagtccccc agggcctgtc    3180
gacacggcgg ggcccggtgg ccggcatctg gccgcacgt gtccgagggg ccccgggtc    3240 cccggcacca tggctactac cggggctccg actacgacga ggccgatggc ccgggcagcg    3300
ggggcggcga ggaggccatg gccgggggcct acgacgcgcc acccccgta cgacacgcgt    3360
```

-continued

```
cctcgggcgc caccgggcgc tcgcccagga ctccccgggc ctcgggcccg gcctgcgcct   3420
cgccttctcg gcacggccgg cgactcccca acggctacta cccggcgcac ggactggcca   3480
ggccccgcgg gccgggctcc aggaagggcc tgcacgaacc ctacagcgag agtgacgatg   3540
attggtgcta agcccgggcg agggaattcc tttttttttt tttttttttt tttttt       3596
```

LARGE SCALE GENOTYPING OF DISEASES AND A DIAGNOSTIC TEST FOR SPINOCEREBELLAR ATAXIA TYPE 6

CROSS-REFERENCE TO RELATED APPLICATION

This is a continuation of application U.S. Ser. No. 09/093,273 filed on Jun. 8, 1998, now abandoned.

This application is a divisional of U.S. Ser. No. 08/779,801, filed Jan. 7, 1997 now U.S. Pat. No. 5,853,995.

FEDERAL FUNDING LEGEND

This invention was produced in part using funds obtained through a grant from the Department of the Army. Consequently, the federal government has certain rights in this invention.

BACKGROUND OF THE INVENTION

1. Field of the Invention

The present invention relates generally to the fields of molecular genetics and diagnosis of genetic diseases. More specifically, the present invention relates to a large scale genotyping of diseases and diagnostic tests and kits for same.

2. Description of the Related Art

Expansion of repeat sequences involving the trinucleotides CAG, CTG, CGG or GAA has been shown to be the primary cause of several neurological disorders[1]. Among them, CAG repeat expansions have been associated with a group of neurodegenerative disorders including Huntington disease[2], spinobulbar muscular atrophy[3], spinocerebellar ataxia type 1 (SCA1)[4], spinocerebellar ataxia type 2 (SCA2)[5-7], spinocerebellar ataxia type 3/Machado-Joseph disease (SCA3/MJD)[8], and dentatorubral-pallidoluysian atrophy/Haw-River syndrome[9]. All these disorders are progressive diseases leading to degeneration of the neurons in central nervous system. The CAG repeats in the respective genes show length polymorphism in the human population, typically, not exceeding 40 repeats. In affected individuals, the expanded alleles contain 36-121 repeats[10].

CAG repeat expansions are much smaller than the hundreds or thousands of repeats often seen in diseases with CGG, CTG, and GAA expansions[11-14]. The expanded CAG alleles show variable degrees of instability in both germline and somatic tissues[15,16]. Intergenerational changes of the CAG repeat size are often biased toward further expansion, particularly if paternally transmitted, providing the molecular basis for anticipation. The CAG repeat arrays in these diseases are located in the coding regions of the involved genes and are translated into polyglutamine tracts in the protein products[17]. It has been postulated that an expansion of the polyglutamine tract produces a gain of function in the protein product in each disease accounting for the dominant inheritance. Based on the relatively uniform characteristics of diseases caused by CAG repeat expansions, it has been speculated that other neurodegenerative diseases with similar clinical characteristics may have expansions of CAG repeats. Indeed, a study by Trottier and colleagues demonstrated that an antibody against a polyglutamine tract detects abnormally large proteins in tissues from patients with either SCA2 or spinocerebellar ataxia type 7 (SCA7), suggesting that the mutation responsible for SCA2 and SCA7 is an expansion of a polyglutamine repeat tract[18].

The prior art is deficient in the lack of effective means for the large scale genotyping of genetic diseases and diagnostic tests and kits for diagnosing such diseases. The present invention fulfills this long-standing need and desire in the art.

SUMMARY OF THE INVENTION

A polymorphic CAG repeat was identified in the human $\alpha_{1A}$ voltage-dependent calcium channel subunit. To demonstrate that expansion of this CAG repeat could be the cause of an inherited progressive ataxia, a large number of unrelated controls and ataxia patients were genotyped. Eight unrelated patients with late onset ataxia had alleles with larger repeat numbers (21-27) compared to the number of repeats (4-16) in 475 non-ataxia individuals. Analysis of the repeat length in families of the affected individuals revealed that the expansion segregated with the phenotype in every patient. Six isoforms of the human $\alpha_{1A}$ calcium channel subunit were identified. The CAG repeat is within the open reading frame and is predicted to encode glutamine in three of the isoforms. Thus, a small polyglutamine expansion in the human $\alpha_{1A}$ calcium channel is most likely the cause of a newly classified autosomal dominant spinocerebellar ataxia, SCA6.

In one object of the present invention, there is provided a method of screening individuals at risk for developing diseases caused by trinucleotide repeat sequence instability, comprising the steps of: amplifying genomic DNA trinucleotide repeat sequences in a sample from an individual by polymerase chain reaction using one or more oligonucleotide primers; restricting said amplified genomic DNA trinucleotide repeat sequences with a restriction enzyme; separating said restricted amplified genomic DNA trinucleotide repeat sequences by electrophoresis to form a sample electrophoresis pattern; labeling a probe capable of detecting said amplified genomic DNA trinucleotide repeat sequences in said sample; hybridizing said sample of restricted, amplified genomic DNA trinucleotide repeat sequences with a first aliquot of said labeled probe under hybridizing conditions to produce a sample hybridization pattern for said sample genomic DNA trinucleotide repeat sequence; amplifying a control genomic DNA trinucleotide repeat sequence by polymerase chain reaction using said one or more oligonucleotide primers, wherein said control genomic DNA trinucleotide repeat sequence is from non-diseased source; restricting said control genomic DNA trinucleotide repeat sequence with a restriction enzyme; separating said restricted control genomic DNA trinucleotide repeat sequence by electrophoresis to form a control electrophoresis pattern; combining said restricted control genomic DNA trinucleotide repeat sequence with a second aliquot of said probe under hybridizing conditions to form a control hybridization pattern for said genomic DNA trinucleotide repeat sequence; comparing said sample hybridization pattern for said sample genomic DNA trinucleotide repeat sequence to said control hybridization pattern for said control genomic DNA trinucleotide repeat sequence; and determining whether said individual to be tested may be at risk for developing diseases caused by trinucleotide repeat sequence instability, wherein if said sample genomic DNA trinucleotide repeat sequence is larger than said control genomic DNA trinucleotide repeat sequence, said individual may be at risk for developing diseases caused by trinucleotide repeat sequence instability.

In another object of the present invention, there is provided a method of identifying genes in which a disease-causing allele is due to trinucleotide repeat sequence instability, comprising the steps of: screening a library with an oligonucleotide having a triplet base repeat; identifying clones which have said triplet base repeat; sequencing said identified clones to determine sequences of nucleotides flanking said triplet base repeat; synthesizing primers complementary to said sequences of nucleotides flanking said triplet base repeat; isolating DNA from a large sampling of individuals, including diseased and non-diseased individuals; amplifying said isolated DNA with said primers to produce amplified triplet base repeat regions; determining a number of triplet base repeats in said triplet base repeat region for each of said individuals in said large sampling; determining whether triplet base repeat expansions are observed at a relatively high frequency in diseased individuals but are absent or occur at very low frequency in non-disease individuals, wherein if triplet base repeat expansions are observed at a relatively high frequency in diseased individuals but are absent or occur at very low frequency in non-disease individuals, it is likely that a disease-causing allele is due to trinucleotide repeat sequence instability.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention may be had by reference to certain embodiments which are illustrated in the appended drawings. These drawings form a part of the specification. It is to be noted, however, that the appended drawings illustrate preferred embodiments of the invention and therefore are not to be considered limiting in their scope.

FIG. 1A shows that all the different isoforms have been observed in at least two independent cDNA clones. The " " represents a 94 base pair nucleotide variation and the " " represents a 36 bp deletion. The site of the GGCAG insertion is indicated by a vertical bar and the position of the glutamine tract (poly Q) is shown as " ". The amino acid changes affected by these variations are shown in FIG. 2. Only the isoforms with the GGCAG insertion have the extended open reading frame. FIG. 1B shows the sequences flanking the stop codon of the human $Ca^{2+}$ channel isoforms BI-1 and BI-1 (GGCAG). The top and bottom letters indicate the respective amino acid encoded by the sequence. The stop codon is indicated by the TAN nucleotide. The nucleotide "N" is a "G" nucleotide which has a decreased size of the "G" peak following an "A" peak, a characteristic of the FS Taq enzyme in dye terminator sequencing chemistry from Applied Biosystem. It was confirmed that this indeed is a "G" nucleotide when the reverse strand was sequenced. The complementary sequence of TAG, CTA is underlined.

FIGS. 2A-2C show the sequence comparison between the rabbit (BI-1) and human $a_1$ voltage-dependent $Ca^{2+}$ channel. FIG. 2A shows the amino acid sequence from 1301 to 1840, FIG. 2B continues the amino acid sequence from 1841 to 2320, and FIG. 2C further continues the amino acid sequence from 2321 to 2528. The partial human cDNA sequence is a combination of two overlapping clones of 3.6 kb representing the largest deduced open reading frame. Identical amino acids are indicated by a "-" symbol and gaps in the alignment are represented by the "." symbol. The human and rabbit BI-1 cDNAs share 90-94% amino acid identity depending on the isoforms. Since the full-length human $\alpha_{1A}$ voltage-dependent $Ca^{2+}$ channel has not been determined, the amino acid strands in the rabbit BI-1 sequence were numbered as reference (OCCCBI-1 in GenBank). Hypothetical insertion of the GGCAG nucleotides into the rabbit BI-1 isoform (accession No X57476) extends its deduced peptide reading frame by 237 amino acids with the stop codon in the rabbit and human at identical positions. In this deduced reading frame the glutamine repeat is underlined starting at amino acid position 2328 in the human and the rabbit cDNA sequences. Without this insertion, the rabbit and human BI-1 isoforms deduced reading frame stops at amino acid position 2273 as indicated by "*" (listed here as 2275 due to introduction of 2 alignment gaps). The amino acids which vary in the isoforms corresponding to the V1, V2, V3 variations and GGCAG insertion are boxed. The V3 isoform has a truncated 3' region with a poly A+ tract. The sequences of the respective isoforms have been deposited in GenBank (accession numbers: U79663, U79664, U79665, U79666, U79667 and U79668).

FIGS. 4A-4D show the analysis of the PCR-amplified products generated with S-5-F1 and S-5-R1 primers flanking the CAG repeat in families with cerebellar ataxia. FIG. 4A shows the expanded allele with 27 repeats in the four affected individuals (I.2, II.3, II.5, and II.7) from the INSCA kindred but in none of the asymptomatic family members. FIG. 4B shows that the expanded allele of 22 CAGs repeats is observed in all five affected members (II.1, II.2, II.3, III.1 and III.2) of the MS2SCA kindred. FIG. 4C shows that in the MDSCA kindred an aberrant size allele of 23 CAG repeat was present in two brothers (II.1 and II.3) and a sister (II.2) with clinical ataxia but not in the asymptomatic daughter of II.1. FIG. 4D shows the SISCA family where two affected members (IV.1 and III.7) separated by five meiotic events share the same number of 22 CAG repeats on their larger alleles. Tracing this allele through the pedigree indicates that their affected progenitors (III.5, II.2, II.4 and I.2) most likely have this expanded allele.

DETAILED DESCRIPTION OF THE INVENTION

Figure 1A:
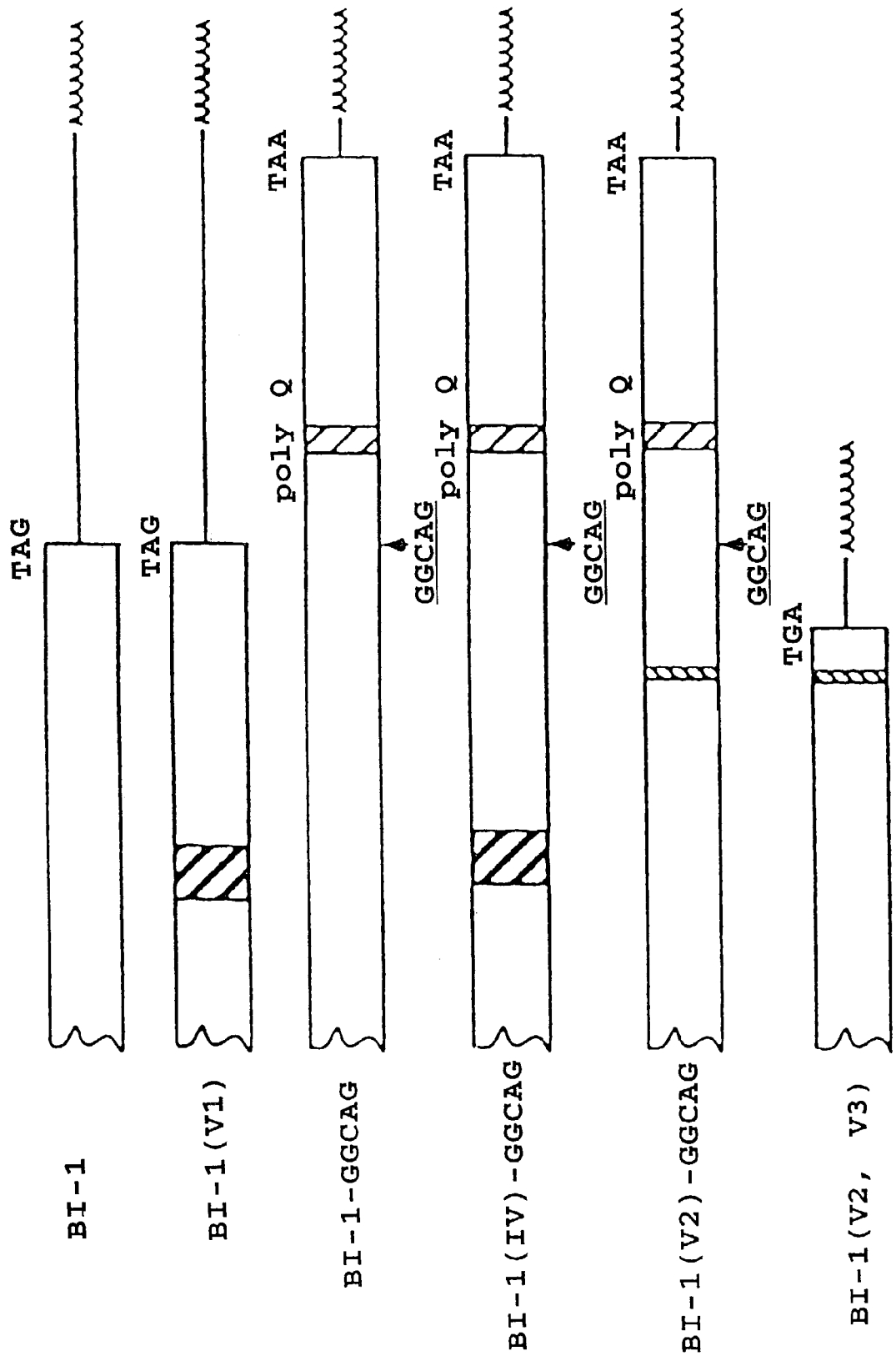
FIGS. 1A-1B show isoforms of the human $\alpha_{1A}$ voltage-dependent $Ca^{2+}$ channel.

The present invention is directed to a method of screening individuals at risk for developing diseases caused by trinucleotide repeat sequence instability, comprising the steps of: amplifying genomic DNA trinucleotide repeat sequences in a sample from an individual to be tested by polymerase chain reaction using one or more oligonucleotide primers; labeling a probe capable of detecting said amplified genomic DNA trinucleotide repeat sequences in said sample; combining said sample of amplified genomic DNA trinucleotide repeat sequences with a first aliquot of said labeled probe under hybridizing conditions to produce a sample hybridization pattern for said sample genomic DNA trinucleotide repeat sequence; amplifying a control genomic DNA trinucleotide repeat sequence by polymerase chain reaction using said one or more oligonucleotide primers, wherein said control genomic DNA trinucleotide repeat sequence is from non-diseased source; combining said control genomic DNA trinucleotide repeat sequence with a second aliquot of said probe under hybridizing conditions to form a control hybridization pattern for said genomic DNA trinucleotide repeat sequence; comparing said sample hybridization pattern for said sample genomic DNA trinucleotide repeat sequence to said control hybridization pattern for said control genomic DNA trinucleotide repeat sequence; and determining whether said individual to be tested may be at risk for developing diseases caused by trinucleotide repeat sequence instability, wherein if said sample genomic DNA trinucleotide repeat sequence is larger than said control genomic DNA trinucleotide repeat sequence, said individual may be at risk for developing diseases caused by trinucleotide repeat sequence instability.

The present invention is additionally directed to a method of identifying genes in which a disease-causing allele is due to trinucleotide repeat sequence instability, comprising the steps of: screening a library with an oligonucleotide having a triplet base repeat; identifying clones which have said triplet base repeat; sequencing said identified clones to determine sequences of nucleotides flanking said triplet base repeat; synthesizing primers complementary to said sequences of nucleotides flanking said triplet base repeat; isolating DNA from a large sampling of individuals, including diseased and non-diseased individuals; amplifying said isolated DNA with said primers to produce amplified triplet base repeat regions; determining a number of triplet base repeats in said triplet base repeat region for each of said individuals in said large sampling; determining whether triplet base repeat expansions are observed at a relatively high frequency in diseased individuals but are absent or occur at very low frequency in non-disease individuals, wherein if triplet base repeat expansions are observed at a relatively high frequency in diseased individuals but are absent or occur at very low frequency in non-disease individuals, it is likely that a disease-causing allele is due to trinucleotide repeat sequence instability.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment. A vector is said to be "pharmacologically acceptable" if its administration can be tolerated by a recipient mammal. Such as agent is said to be administered in a "therapeutically effective amount" if the amount administered is physiologically significant. An agent is physiologically significant if its presence results in a change in the physiology of a recipient mammal. For example, in the treatment of retroviral infection, a compound which decreases the extent of infection or of physiologic damage due to infection, would be considered therapeutically effective.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15-25 or more nucleotides, although it may contain fewer nucleotides.

As used herein, the terms "restriction endonucleases" and "restriction enzymes" refer to bacterial enzymes, each of which cut double-stranded DNA at or near a specific nucleotide sequence.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The following examples are given for the purpose of illustrating various embodiments of the invention and are not meant to limit the present invention in any fashion.

EXAMPLE 1

Isolation of S-5 cDNA

The isolation of the S-5 cDNA was carried out by screening a primary human brain CDNA library with a radiolabeled oligonucleotide probe (GCT)$_7$. The human brain cDNA was oligo-d(T) primed using Guber and Hoffman methodology[44] with mRNA purchased from Clontech (Palo Alto, Calif.). The cDNA library was constructed with Not I restriction linker for cloning into IZAP II vector. The library was plated at a density of 1000 plaques per 150 mm Luria broth agar plates. A total of 150,000 primary clones were screened. Hybridization with a radiolabeled oligonucleotide probe (GCT)$_7$ was carried out at 55° C. using standard aqueous hybridization solution[45]. The filters were washed 3 times for 30 minutes each at 55° C. in 2×SSC and 0.1% SDS. Hybridizing clones were purified for plasmid rescue. Plasmid DNAs was isolated using an AutoGen 740 instrument and were sequenced using ABI kit and protocol on a ABI-373A sequencer. Sequencing of the cDNAs were carried out to confirm the presence of the triplet repeat sequence. The S-5 cDNA was one out of the 387 unique recombinant cDNAs obtained by this approach. Additional clones of the $\alpha_{1A}$ calcium channel were isolated by using the S-5 cDNA as probe. In addition to the above human brain cDNA library, a commercial human fetal brain cDNA library with Eco RI cloning site from Strategene (La Jolla, Calif.) was screened and the identified clones from the library were used to reconstruct the 3' region from the Not I site to the poly (A) tract.

EXAMPLE 2

PCR Analysis

The degree of CAG length polymorphism in the $\alpha_{1A}$ calcium channel was determined by the following primers: S-5-F1 (5'-CACGTGTCCTATTCCCCTGTGATCC-3') (SEQ ID NO:1) and S-5-R1 (5'-TGGGTACCTC-CGAGGGCCGCTGGTG-3') (SEQ ID NO:2), though any appropriate primers based on the sequence of the $\alpha_{1A}$ calcium channel gene may be used for this purpose. For each reaction, 5 pmol of each primer was end-labeled with 1 mCi of [$\gamma$-$^{32}$P]ATP using 0.05 unit of polynucleotide kinase for 30 minutes. Each PCR analysis contained 20 ng of genomic DNA mixed with 5 pmol each of radiolabeled S-5-R1 and S-5-F1 primers in a total volume of 25 ml containing 0.25 unit of Taq polymerase, 125 µM dNTP, 10 mM Tris pH 8.9, 2.5 mM MgCl$_2$, 30 mM KCl, and 3.5% (V/V) glycerol. The samples were denatured at 95° C. for 3 minutes, followed by 28 cycles of denaturation (94° C., 25 seconds), annealing (68° C., 30 seconds) and extension (72° C., 2 minutes). Fifteen ml of formamide loading dye was added to the reaction, the mixture was denatured for 20 minutes at 95° C. Seven ml were electrophoresed through a 6% polyacrylamide/8 M urea gel. Alleles sizes were determined by comparing migration relative to an M13 sequencing ladder. Control DNAs used included 65 samples from the CEPH families; 125 unrelated controls provided by various colleagues in the department of Molecular and Human Genetics; 160 samples from diabetic sibling pairs; 41 sporadic breast cancer cases; 42 from Parkinson index cases; 24 from dystonia index cases and 18 sporadic Alzheimer cases.

EXAMPLE 3

Northern Analysis

The northern blot containing poly A$^+$ RNA from multiple human tissues was purchased from Clonetech. 200 ng of S-5 cDNA insert was radiolabeled with [$\alpha$-$^{32}$P]dCTP using a random labelling kit from Pharmacia. The probe was hybridized overnight at 65° C. according to the protocol recommended by Clonetech. The filter was washed 3 times at 68° C. for 30 minutes each in 0.1×SSC, 0.1% SDS and then exposed to X-ray film. Lower stringency washes at 68° C. at 0.5×SSC and 0.1% SDS gave many more bands in different tissues suggesting cross reaction with other calcium channel genes.

EXAMPLE 4

Linkage Analysis

Inspection of the genotype data shows a clear association between an increased number of CAG repeats and the ataxia phenotype. Of the 133 ataxia patients, eight had repeat lengths greater than 20, whereas none of the controls had repeat lengths greater than 16. This association was assessed statistically using a 2×2 table comparing the presence of expansions in ataxia cases versus controls. The level of significance was determined using Fisher's exact test.

Haplotype analysis was used to show that the expansion and disease are transmitted together. To model the situation of a single locus with both a phenotype (ataxia) and a polymorphism (expansion): two loci were used, one disease locus and one polymorphism, completely linked and in complete linkage disequilibrium. The haplotype frequencies were calculated by assuming all 133 of the cases suffer from some kind of dominantly inherited ataxia. There should, therefore, be one disease causing mutation for each case. Eight of these mutations (approximately 6%) were caused by CAG repeat expansions; the other 94% were caused by other mutations, either non-expansion mutations in this gene or mutations in other genes. The additional information needed to calculate the haplotype frequencies is the population frequency of dominant ataxia at unknown loci. The higher the estimate of this frequency the lower the lod scores. A conservative number of 1 in 500 was used for this analysis which places the gene frequency at 1 in 1000. The four haplotype frequencies are then: 0.999 (no ataxia-no expansion), 0.0 (no ataxia-expansion), 0.00094 (ataxia-no expansion), and 0.00006 (ataxia-expansion). These haplotype frequencies were used to calculate the lod scores in the four ataxia families using the FASTLINK version 3.0P software programs. The affection status and genotypes were set for all patients, while unaffected and ungenotyped individuals were specified as unknown affected status and unknown genotype.

To identify diseases which are caused by an expansion of a CAG repeat, a large scale genotyping survey was performed on using polymorphic CAG repeats and DNA samples from patients with late onset neurodegenerative diseases. The present invention reports that the human homolog of the rabbit $\alpha_{1A}$ voltage-dependent calcium channel BI-1 gene contains a polymorphic CAG repeat sequence which is expanded in a fraction of patients diagnosed with autosomal dominant cerebellar ataxia. These results indicate that the expansion of a CAG repeat predicted to encode for polyglutamine in the human $\alpha_{1A}$ voltage-dependent Ca$^{2+}$ channel gene is the apparent cause for one form of cerebellar ataxia.

EXAMPLE 5

CAG Repeats in the Human $\alpha_{1A}$-Calcium Channel Subunit

To identify genes containing trinucleotide repeat sequences, an unamplified human brain cDNA library was screened using a $(GCT)_7$ repeat oligonucleotide as a probe. This screen identified 387 cDNA clones determined to be independent based on sequence analysis. The repeat sizes in these clones ranged from 4 to 21. Partial cDNA clones corresponding to the dentatorubral-pallidoluysian atrophy/Haw-River[9] and Machado-Joseph disease[8] genes were isolated in this screen. cDNA clones corresponding to the SCA1, SCA2, and Huntington disease genes were not isolated in this screen, most likely because the CAG repeat in each of these genes is located in the 5' region of a large transcript and the cDNA library screened is biased for 3' cDNA termini given that it was generated using oligo-d(T) priming.

The first clone examined extensively was a cDNA designated S-5 that contained 13 CAG repeats. The deduced peptide sequence of this 1.2 kb cDNA has 90% amino acid identity to the BI-1 isoform of the rabbit $\alpha_{1A}$ voltage-dependent $Ca^{2+}$ channel (also known as P/Q-type $Ca^{2+}$ channel) suggesting that the S-5 clone is a partial cDNA of the human homolog[19]. The deduced human peptide sequence is also 90% identical to the rat brain $\alpha_{1A}$ $Ca^{2+}$ channel subunit[20]. Partial human cDNA sequence corresponding to rabbit BI-1 amino acid position 722-1036 was previously reported to share 92% and 82% with the rabbit and rat $\alpha_{1A}$ subunit of calcium channel, respectively[21]. The cDNA of the present invention contains coding sequence which corresponds to the carboxy terminus region of the rabbit protein beginning at amino acid position 1325. The sequence data suggest that the cDNA isolated encodes the human $\alpha_{1A}$ subunit of the calcium channel.

Using the somatic cell hybrid mapping panel #2 from Corriel, the $\alpha_{1A}$ $Ca^{2+}$ channel was localized to human chromosome 19 by sequence tag site (STS) mapping. Diriong et al.[22], have reported the mapping of the $\alpha_{1A}$ $Ca^{2+}$ channel subunit to human chromosome 19p13 using a partial cDNA clone. The gene symbol of this locus was designated CACNL1A4[22]. A partial human cDNA, (corresponding to rabbit BI-1 nucleotide position 6487-7165) of the CACNL1A4 gene was reported by Margolis et al.[23] and was shown to map to chromosome 19. A report describing the full-length sequence of the human CACNL1A4 gene was published recently by Ophoff and collegues[24].

In rabbit, two isoforms (BI-1 and BI-2) of the $\alpha_{1A}$ calcium channel subunit have been identified[19]. These isoforms differ from each other in the carboxy terminus sequence where BI-2 has an additional 151 amino acids. These isoforms are believed to result from an insertion-deletion of 423 nucleotides. The presence of the 423 nucleotides in BI-1 introduces a stop codon which leads to the shorter, 2273 amino acid isoform. In rat brain, at least four alternatively spliced isoforms of the $\alpha_{1A}$ $Ca^{2+}$ channel gene have been observed, but the sequence of only one isoform has been reported[20].

Figure 1B:
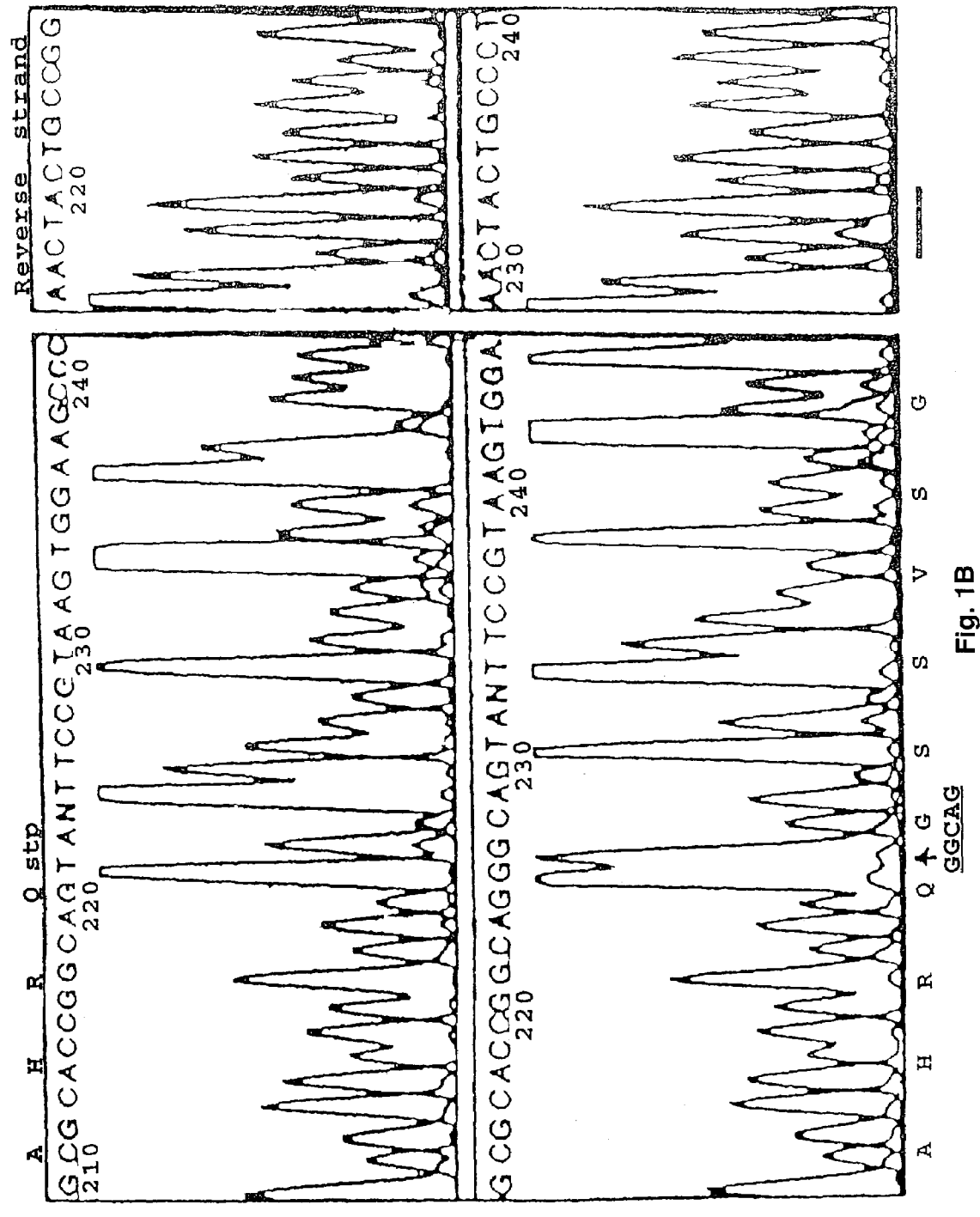

Comparison between the rabbit and human sequences revealed that the CAG repeat was conserved and was located in the deduced 3' untranslated region of the rabbit $\alpha_{1A}$ $Ca^{2+}$ channel BI-1 and the S-5 cDNAs. The finding of a high degree of identity (84% identity over 700 nucleotides) between the 3' untranslated region of the rabbit BI-1 isoform and the human S-5 clone of the present invention, raised the possibility that additional splice variants may occur and that some may contain an open reading frame in which the CAG repeat is translated. To examine this, the primary human cDNA library and a commercial fetal brain cDNA library was rescreened using the S-5 cDNA as probe. In total, 17 additional clones were isolated, and careful sequence analysis of these clones allowed identification of several alternatively spliced isoforms of the carboxyl region of the human $\alpha_{1A}$ $Ca^{2+}$ channel (FIG. 1A). In particular, five of these cDNAs contain a 5 base pair (GGCAG) insertion prior to the TAG stop codon of the S-5 cDNA (FIG. 1B). Clones with this 5 base pair insertion have an extended deduced open reading frame of an additional 239 amino acids in the human gene. Hypothetical insertion of this 5 base pair sequence into the rabbit BI-1 calcium channel at amino acid position 2273 extends its deduced reading frame by 237 amino acids, and the peptide homology to the human sequence remains highly conserved (80% identity) arguing for the presence of such an isoform in the rabbit brain (see FIG. 2). In this BI-1 (GGCAG) isoform, the CAG repeat encodes for polyglutamine starting at amino acid position 2328 in the human and rabbit $\alpha_{1A}$ calcium channel gene.

Additional isoforms of the human $\alpha_{1A}$ $Ca^{2+}$ channel gene were also observed in the other clones. To ensure that none of these resulted from cloning artifacts, at least two independent clones for each isoform were isolated and sequenced. In total, six variants were observed including the variant identical to the rabbit BI-1 isoform also designated BI-1 for human. The variant designated BI-1(V1) has a 94 base pair sequence which differs at the nucleotide level from BI-1 but is homologous at the amino acid level. This variant has also been described in rabbit[19]. The BI-1(V1) isoform isolated in this study is 99.8% identical to the deduced peptide sequence described by Ophoff et al.[24]. There are three differences involving amino acids at positions 1460 (Ala to Gly), 1605 (Ala to Val), and 1618 (Ala to Val). The amino acids at these positions in the deduced sequence are consistent in several clones analyzed and are identical to the rabbit and rat $\alpha_{1A}$ $Ca^{2+}$ channel subunit deduced amino acids. The BI-1 and the BI-1(V1) isoforms are observed in combination with the GGCAG insertion (SEQ ID No. 3 and SEQ ID No. 4). Additional splice variants include BI-1(V2)-GGCAG (SEQ ID No. 5) which has a 36 nucleotide deletion and a variant with a truncated 3' region BI-1-(V2,V3) (FIG. 1A). The identified clones have different combinations of these variants with identical flanking sequences in the non variant segment thereby ruling out cloning artifacts.

Figure 3:
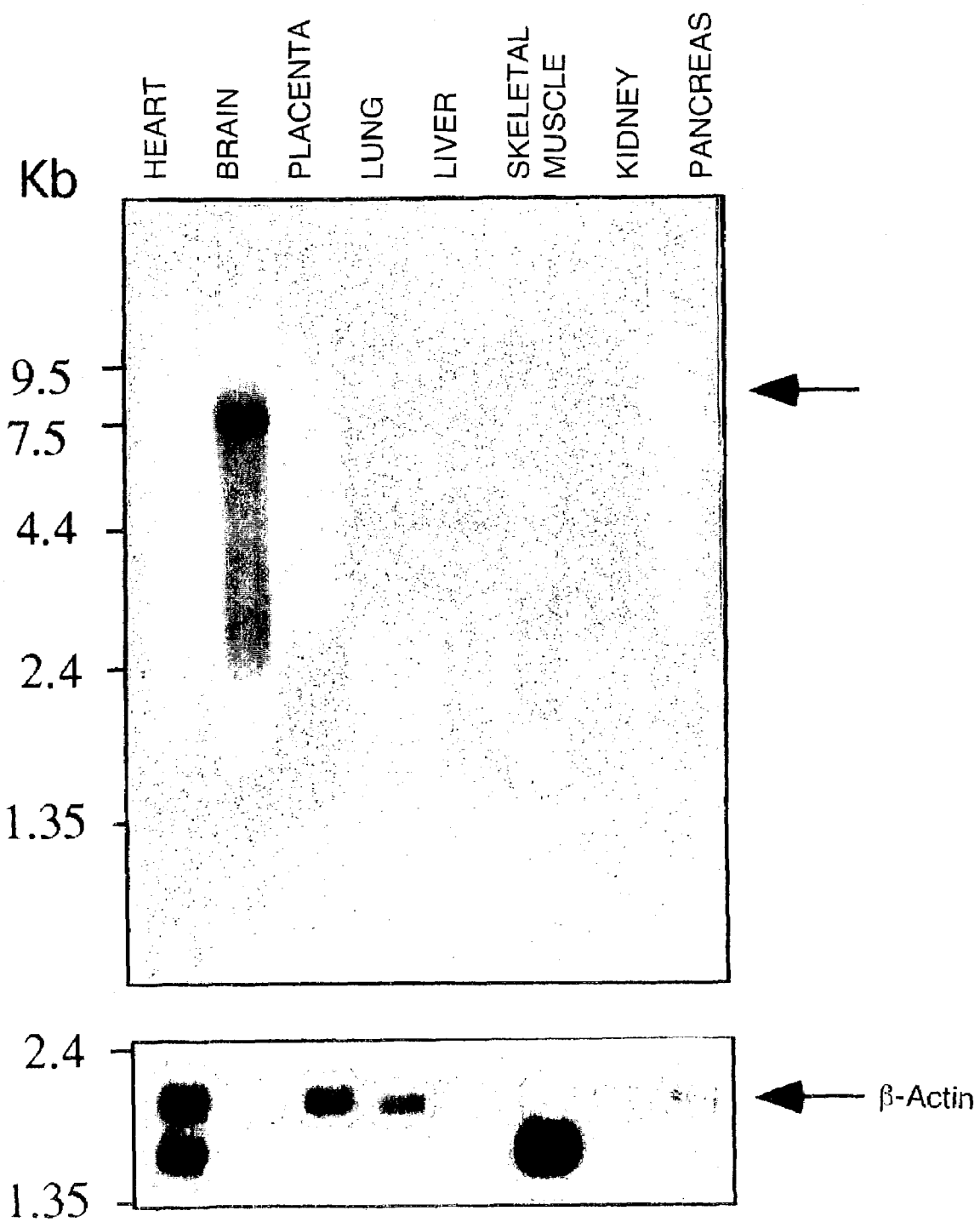
FIG. 3 shows the northern analysis of human $\alpha_{1A}$ voltage-dependent $Ca^{2+}$ channel expression. Hybridization was carried out with the S-5 cDNA as probe. A distinct band of 8.5 kb was present in brain mRNA with a smear pattern specific to this probe and not detected using the $\beta$-actin probe. The smearing in the mRNA from brain may reflect cross hybridization with the various alternative spliced forms or some degradation.

Consistent with the presence of multiple isoforms, northern analysis at high hybridization stringency with the S-5 cDNA gave a single band of 8.5 kb overlaying a smear above and below the predominant size mRNA in brain (FIG. 3). At lower hybridization stringency, many additional bands were observed in all tissues suggesting cross hybridization to other types of calcium channels (data not shown). All of the clones from this human brain library, which range from 1.2 to 3.1 kb in size, represent only the carboxyl region of the human $\alpha_{1A}$ $Ca^{2+}$ channel subunit. The CAG repeat in the respective adult brain cDNAs which were derived from a single human mRNA source contained either 11 or 13 repeats, suggesting the representation of polymorphic CAG alleles transcribed from the homologous chromosome pair.

EXAMPLE 6

Large Scale Genotyping Survey for Expanded CAG Repeats

The possibility of identifying aberrant length CAG repeat sequences distinguishable from normal length polymorphism in the human $\alpha_{1A}$ Ca$^{2+}$ channel subunit was examined via a large scale genotyping survey of ataxia patients. This technique is based on the premise that if trinucleotide expansion is responsible for SCA6, expansions would be observed at a relatively high frequency in affected individuals but would be absent or occur at very low frequency in non-disease alleles.

DNA samples from 475 unrelated non-ataxia individuals in the general population and 133 DNA samples from unrelated index cases known to have progressive cerebellar ataxia were analyzed. Using a pair of radiolabeled synthetic oligonucleotide primers flanking the CAG repeat sequence of the human $\alpha_{1A}$ Ca$^{2+}$ channel subunit, the CAG repeat region of each sample was amplified and the size of the CAG repeat region was determined via gel electrophoresis. The repeat sizes of the ataxia group samples were compared with those obtained from the DNA of the general population samples.

Table 1 shows the distribution of the CAG repeat sizes in the $\alpha_{1A}$ Ca$^{2+}$ channel subunit gene of the 133 index patients with cerebellar ataxia as well as the distribution of the CAG repeat sizes in the $\alpha_{1A}$ Ca$^{2+}$ channel subunit gene of the 475 non-ataxia samples. The ethnic background of the control and patient populations included individuals of Caucasian, African American, Hispanic and Asian ancestry. Individuals from the general population displayed 10 alleles ranging from 4 to 16 CAG repeat units and a heterozygosity of 71%. In the cerebellar ataxia patients, the number of CAG repeats ranged in size from 7 to 27 with a heterozygosity of 74%. As can be seen in the allele size distribution, eight unrelated patients out of 133 ataxia index cases (6%) had a larger size allele of at least 21 CAG repeat units. Although the expansion was relatively small it was not observed in 475 individuals from the non-ataxia controls making it extremely unlikely to be normal length polymorphism (P<10$^{-5}$ using Fisher's exact test).

TABLE 1

Comparison of the number of CAG repeat units on Ataxia and Non-Ataxia chromosomes

| Number of CAG repeat units | Non-ataxia controls Number of chromosomes | Ataxia index controls Number of chromosomes |
|---|---|---|
| 4 | 21 | 0 |
| 5 | 0 | 0 |
| 6 | 4 | 0 |
| 7 | 65 | 27 |
| 8 | 2 | 2 |
| 9 | 0 | 0 |
| 10 | 0 | 0 |
| 11 | 398 | 91 |
| 12 | 150 | 57 |
| 13 | 264 | 73 |
| 14 | 39 | 7 |
| 15 | 6 | 1 |
| 16 | 1 | 0 |
| 17 | 0 | 0 |
| 18 | 0 | 0 |
| 19 | 0 | 0 |
| 20 | 0 | 0 |
| 21 | 0 | 1 |
| 22 | 0 | 5 |
| 23 | 0 | 1 |
| ... | ... | ... |
| 27 | 0 | 1 |

The genomic DNA from these eight index cases was amplified by the S-5 primers, subcloned and sequenced. The number of CAG repeat units obtained from sequence analysis was consistent with an increase in the number of pure CAG repeat units in the $\alpha_{1A}$ Ca$^{2+}$ channel subunit. The different number of CAG repeat units in these expanded alleles argues against a rare founder allele. The observation of aberrant alleles of expanded sizes in the ataxia population and their absence in the general population was consistent with the possibility that these expanded alleles represent the mutational basis in a fraction of the ataxia patients analyzed.

The method of large scale genotyping was effective in identifying the CAG expansin in the $\alpha_{1A}$ Ca$^{2+}$ channel subunit gene. Thus, this concept may be used in the search for other mutation types associated with triplet repeat disease phenomenon. Basically, one assumes that trinucleotide repeat expansion is associated with alleles at high frequency in disease phenotypes, but absent or at low frequency in non-disease phenotypes. Large scale genotyping, thus, is different from the approaches used for the identification of other human disease genes, including the positional cloning approach. In the positionaly cloning approach, a genetic linkage to a specific chromosomal region must be established prior to the isolation of the candidate disease gene. Positional cloning was used for the identification of the genes for Huntington disease, spinobulbar muscular atrophy, spinocerebellar ataxia type 1, spinocerebellar ataxia type 2, spinocerebellar ataxia type 3/Machado-Joseph disease, and the genes associated with Fragile X and myotonic muscular dystrophy.

The approach of the present invention also is different from random candidate gene approach for human disease, whereby no systematic strategy is used in the identification of genes. The random candidate gene approach was used in the identification of the dentatorubral-pallidoluysian atrophy/Haw-River syndrome gene. The strategy of the present invention is based on the observation that triplet repeat sequences in disease genes are polymorphic in length which makes them suitable for a large scale genotyping survey. The large scale genotyping approach identifies aberrant allele sizes in diseased individuals as compared with the non-disease population. This concept-driven strategy negates the need for prior establishment of specific genetic association (linkage) in family pedigrees as is employed as a first step in a positional cloning. The large scale genotyping strategy of the present invention is a direct-gene-to-disease-state approach.

In another object of the present invention, there is provided a method of identifying genes in which a disease-causing allele is due to trinucleotide repeat sequence instability, comprising the steps of: screening a library with an oligonucleotide having a triplet base repeat; identifying clones which have said triplet base repeat; sequencing said identified clones to determine sequences of nucleotides flanking said triplet base repeat; synthesizing primers complementary to said sequences of nucleotides flanking said triplet base repeat; isolating DNA from a large sampling of individuals, including diseased and non-diseased individuals; amplifying said isolated DNA with said primers to produce amplified triplet base repeat regions; determining a number of triplet base repeats in said triplet base repeat region for each of said individuals in said large sampling; determining whether triplet base repeat expansions are observed at a relatively high frequency in diseased individuals but are absent or occur at very low frequency in non-disease individuals, wherein if triplet base repeat expansions are observed at a relatively high frequency in diseased individuals but are absent or occur at very low frequency in non-disease individuals, it is likely that a disease-causing allele is due to trinucleotide repeat sequence instability.

EXAMPLE 7

Inheritance of Expanded Alleles in Ataxia Patients

Four of the index cases were from families where additional affected members have been clinically evaluated, and DNA could be obtained for genotypic analysis. Twenty-one family members participated in the study after informed consents were obtained. Fourteen of the 21 had clinical evidence of ataxia. In each of these families, the ataxia was inherited in an autosomal dominant manner with the age of onset ranging between 28 and 50 years.

Figure 4A:
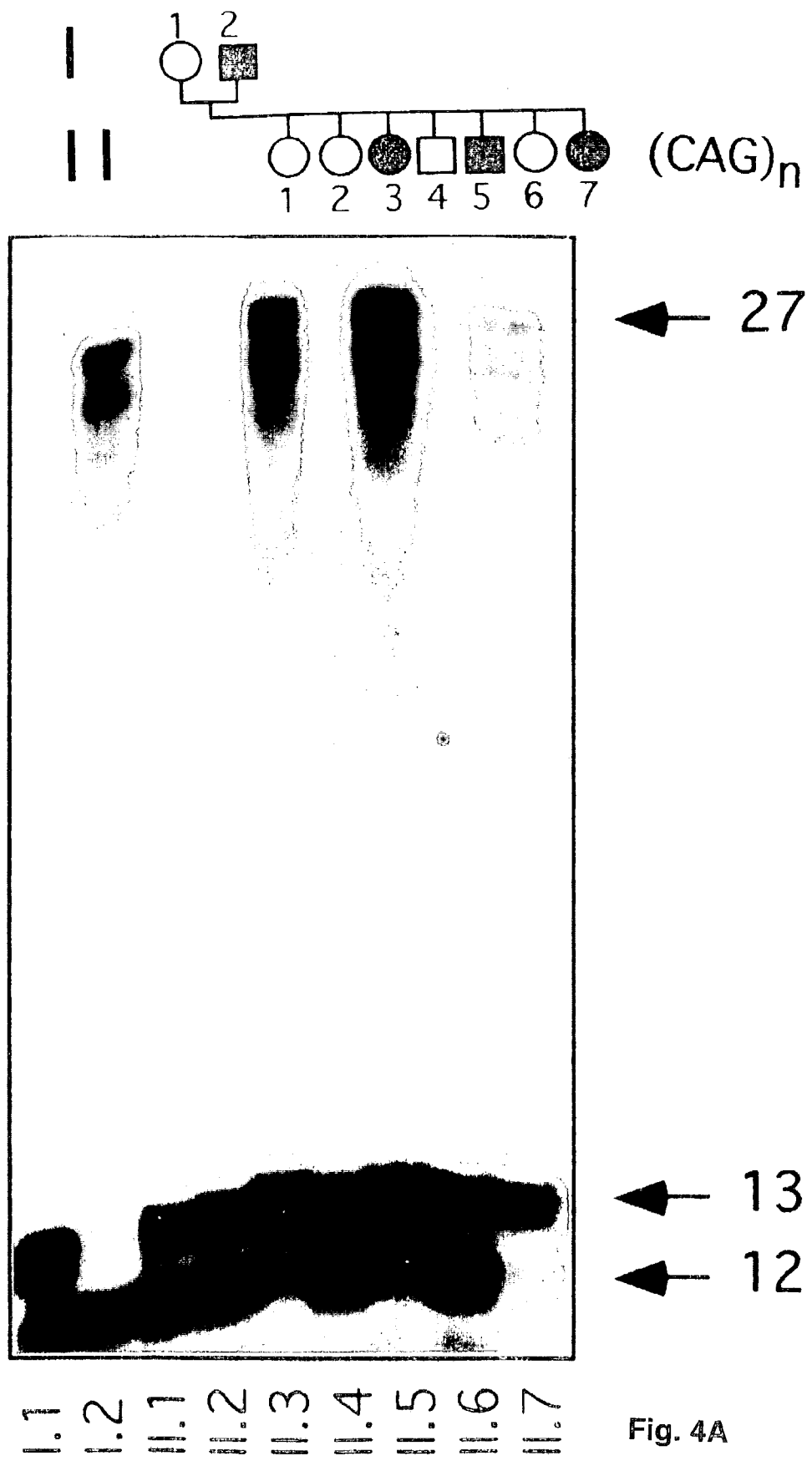
Figure 4C:
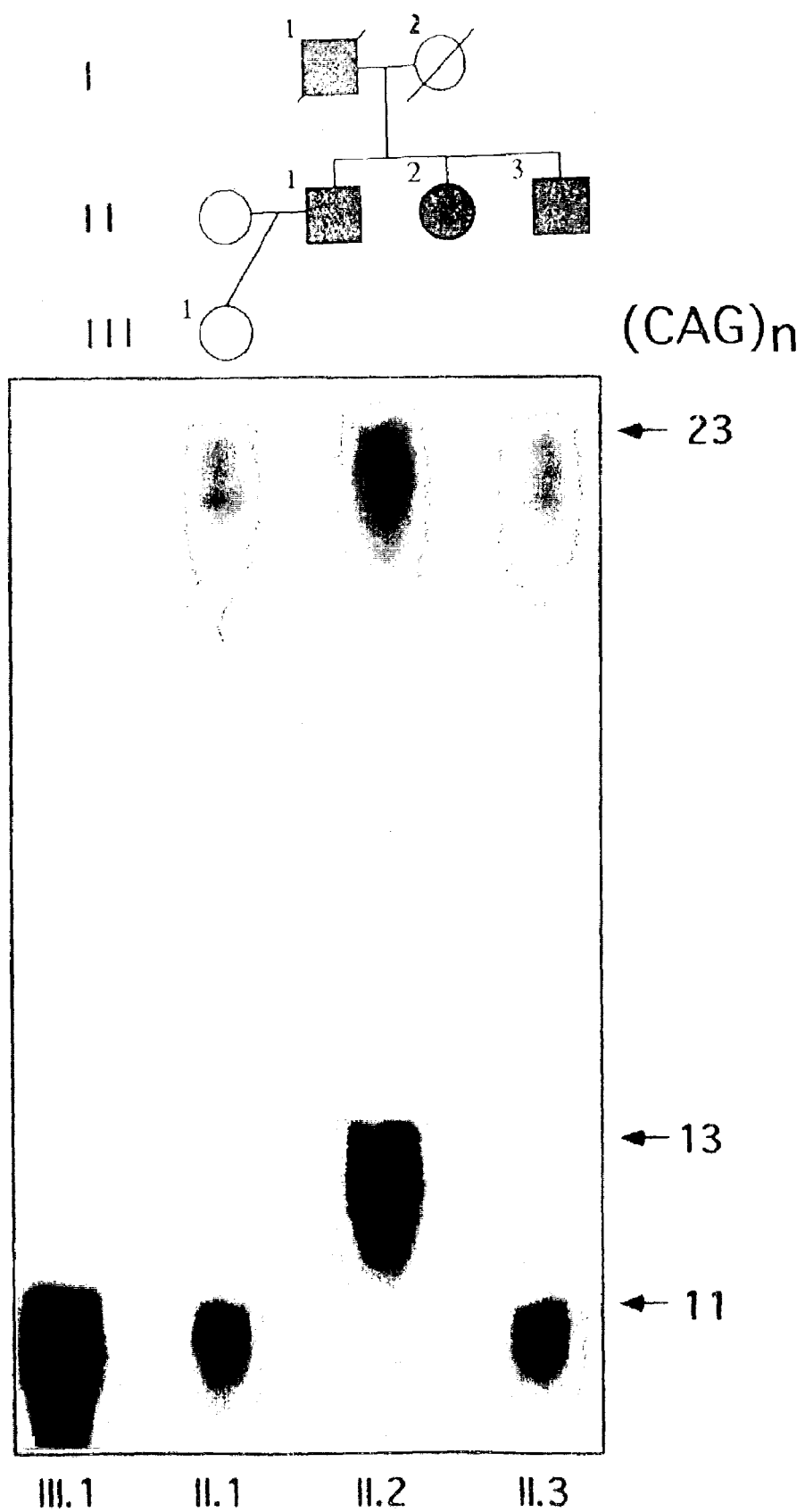

Genotypic analyses of family members using the S-5 primers demonstrated that the expanded allele segregated with the disease phenotype in each family. For example, FIG. 4A shows the expanded allele with 27 repeats in the four affected individuals from the INSCA kindred but in none of the asymptomatic family members including a distantly related member (data not shown). In this kindred the age of onset ranged between 28 and 31 years, and three of the asymptomatic individuals were 41 years old or older. FIG. 4B shows that the expanded allele of 22 repeats was observed in all five affected members of the MS2SCA kindred. In the MDSCA kindred (FIG. 4C) an aberrant size allele of 23 CAG repeat was present in two brothers (II.1 and II.3) and a sister (II.2) with clinical ataxia but not in the asymptomatic daughter of II.1. In the SISCA family, shown in FIG. 4D, two affected members (IV.1 and III.7) separated by five meiotic events share the same number of 22 CAG repeats on their larger alleles. Tracing this allele through the pedigree indicates that their affected progenitors (III.5, II.2, II.4 and I.2) most likely have carried this expanded allele. The segregation of the expanded allele with the disease in these families is highly significant as evident by a cumulative haplotype lod score of 5.08 at a recombination frequency of zero when the genotypic data from affected individuals were analyzed using version 3.0P of the FASTLINK computer programs (see above)[26,27]. The lod scores for each kindred are summarized in TABLE 2. Taken together, the statistically significant finding that the expanded alleles are only observed in patients diagnosed with cerebellar ataxia but not in 475 non-ataxia controls and the clear cut association of these expanded alleles with disease demonstrate that the polyglutamine expansion in the $\alpha_{1A}$ voltage-dependent $Ca^{2+}$ channel subunit is the cause of this late onset dominantly inherited ataxia.

TABLE 2

Lod scores from haplotype analysis

| Family | Lod score at Theta = 0 |
|---|---|
| INSCA | 1.20 |
| MDSCA | 0.90 |
| MS2SCA | 1.49 |
| SISCA | 1.49 |
| SUM | 5.08 |

EXAMPLE 8

Clinical and Pathological Findings in Patients with CAG Repeat Expansion

The clinical features of the patients in the above-described families were very similar and consist predominantly of mild but slowly progressive cerebellar ataxia of the limbs and gait, dysarthria, nystagmus, and mild vibratory and proprioceptive sensory loss. The disease is very insidious and most patients do not realize they are affected initially but do describe a sense of momentary imbalance and "wooziness" when they take a quick turn or make a rapid movement. Typically, it is years after this initial sensation when the patients realize that they have developed permanent balance and coordination difficulties. The disease usually progresses over 20-30 years leading to impairment of gait and causing the patient to become wheel-chair bound. In the few older patients, choking has been observed suggesting involvement of the brain stem, and the disease has been the cause of death in several members of the MDSCA and MS2SCA kindreds. Symptoms develop generally when the patients are in their forties in the MDSCA, SISCA, and MS2SCA families where the repeat number is 22-23; however in the INSCA kindred where the expanded allele contains 27 repeats, the disease onset is between 28 and 31 years in all the affected individuals. Magnetic resonance imaging of the brain in affected individuals reveals isolated cerebellar atrophy. Detailed neuropathologic studies on two deceased members from the SISCA kindred showed marked cerebellar atrophy and very mild atrophy of the brain stem[28]. Microscopic examination revealed severe loss of cerebellar Purkinje cells, moderate loss of granule cells and dentate nucleus neurons, and mild to moderate neuronal loss in the inferior olive.

The hereditary cerebellar ataxias are a clinically and genetically heterogenous group of neurological disorders associated with dysfunction of the cerebellum and its afferent and efferent connections. To date, six autosomal dominant spinocerebellar ataxias (SCAs) have been mapped to human chromosomes 6, 12, 14, 16, 11, and 3 with the loci designated SCA1, SCA2, SCA3, SCA4, SCA5, and SCA7, respectively[10]. The map location of the genes in many families with dominantly inherited and progressive ataxias remains unknown. The mapping of the $\alpha_{1A}$ $Ca^{2+}$ channel subunit to human chromosome 19p13 and the identification of the CAG repeat expansion in this channel as the mutational mechanism in four families define a new SCA locus on human chromosome 19p13 which can be designated SCA6.

In the past, the term SCA6 has been used to described dominantly inherited SCAs that did not map to any of the known loci[29,30]. This mapping nomenclature was revised to assign the SCA6 locus to the dominantly inherited ataxia mapping to chromosome 19p13 (HGM Nomenclature Committee). Hereditary paroxysmal cerebellar ataxia (HPCA) or episodic ataxia (EA) has also been mapped to the 19p13 region[31-32]. The locus for another episodic disease, familial hemiplegic migraine (FHM)[33], has been localized to 19p13 in the region where the gene for HPCA/EA was assigned. Patients with HPCA or EA typically have periodic ataxia with apparently normal coordination between attacks. This is reminiscent of the episodic sensation of unsteadiness described in patients years before the ataxia becomes a permanent finding. The only persistent abnormality on neurologic exam in HPCA/EA is the presence of nystagmus, a finding seen in all the patients. Brain imaging studies revealed that some HPCA/EA patients have cerebellar atrophy[31]. Interestingly, in several families with FHM, affected members have shown degenerative cerebellar atrophy which is associated with ataxia, nystagmus and other vestibulocerebellar ocular abnormalities, similar to those seen in HPCA/EA[34]. The overlap in the phenotypes of these two disorders led to the hypothesis that HPCA/EA and FHM are allelic disorders possibly caused by a mutation in an ion channel gene because of the periodic nature of the symptoms[32,34].

Recently, Ophoff et al. reported four missense mutations in the human $\alpha_{1A}$ Ca$^{2+}$ channel subunit gene in families with FHM and two mutations disrupting the reading frame of the same gene in two families with EA[24]. These results and the present invention demonstrate that FHM, HPCA/EA and the progressive SCA6 are allelic disorders. The nature of the mutation (CAG repeat expansion in SCA6 versus protein truncation in HPCA/EA) affects the clinical course of the disease. Permanent and progressive cerebellar and brain stem dysfunction were observed in SCA6 whereas mild and intermittent cerebellar dysfunction was seen in HPCA/EA. This suggests that the glutamine expansion affects the function of the channel in a manner which triggers progressive neuronal loss. This may be via alteration of neurotransmitter release or by causing abnormal levels of intracellular Ca$^{2+}$ leading to subsequent cell death[21,35]. At this time the pathogenic effects of each of these mutations with regard to periodic neurological dysfunction versus permanent and progressive disease cannot be determined and will have to await transgenic mouse models and neurophysiologic studies. Although other mutations in the CACNL1A4 gene in SCA6 families has not been excluded, the highly significant association between expansion and disease phenotype (P<10$^{-5}$) in eight independent ataxia families and the different number of repeats on expanded alleles in four families (in the absence of intergenerational instability) argue strongly that this is the disease causing mutation. It is also important to note that Ophoff and collegues[24] did not observe any expanded alleles in the 50 normal individuals they genotyped.

Although the mutational mechanism in SCA6 proved to involve an expansion of a translated CAG repeat like the other dominantly inherited progressive ataxias, it is not clear whether the pathogenic mechanism is similar. There are two key differences between the mutation in SCA6 and those causing SCA1, SCA2, SCA3, HD, DRPLA, and SBMA. First, the expanded mutant alleles in SCA6 (21-27 repeats) are remarkably smaller than the expanded alleles seen in any of the other neurodegenerative diseases (36-121 repeats) and are well within the normal range of polyglutamine tracts seen at the other loci in many unaffected individuals. Second, the CAG repeat expansion occurs in the coding region of a gene which is known to be important for normal Purkinje cell function and survival[19,25]. This raises the possibility that the CAG expansion is exerting its pathogenic effect by directly interfering with the normal function of the $\alpha_{1A}$ calcium channel.

Voltage-dependent calcium channels mediate the entry of calcium into neurons and other excitable cells and play important roles in a variety of neuronal functions, including membrane excitability, neurotransmitter release, and gene expression[36]. Calcium channels are multisubunit complexes with the channel activity mainly mediated by the pore-forming $a_1$ subunit, however, additional subunits including b, a$_2$/d, and g act as accessory proteins that regulate channel activity[36-38]. The cDNAs encoding six $a_1$ genes have been cloned and have been designated $\alpha_{1A,B,C,D,E}$ and S[39]. The human gene characterized in the present invention is most homologous to the rabbit and rat $\alpha_{1A}$ isoforms[19,20]. The mapping assignment to human chromosome 19 is consistent with the previous mapping of the human sequence encoding the $\alpha_{1A}$ isoform to chromosome 19p13[22-24]. A combination of electrophysiologic and pharmacologic properties define four main types of high-threshold calcium channels in peripheral and central neurons of mammals[40]. These are designated L, N, P, and Q, with the P-type channels being the predominant calcium channel in Purkinje cells, and the Q type being a prominent calcium current in cerebellar granule cells[25,38]. The cloned $\alpha_{1A}$ isoform has been shown to give rise to P and/or Q type calcium currents[38,40]. The additional isoforms identified may help resolve some of the functional differences observed for the P/Q type calcium currents. The pharmacologic as well as the electrophysiologic properties of the $\alpha_{1A}$ channel, together with its abundant expression in rat cerebellum emphasize its importance for calcium entry and homeostasis in Purkinje cells[25,41].

Recently, the mouse homolog of the a$_{1A}$ voltage-dependent subunit gene has been identified using a positional cloning strategy aimed at identifying the gene mutated in the tottering (tg) and leaner (tg$^{la}$) mice which show seizures and cerebellar ataxia[42]. This locus maps to mouse chromosome 8 in a region syntenic with human 19p13. The tg mutation, a C to T change at position 1802, causes a nonconserved proline to leucine substitution in a position very close to the conserved pore-lining domain in the extracellular segment of the second transmembrane domain. This mutation leads to a recessive neurological disorder with ataxia, motor- and absence-type seizures.

The tg$^{la}$ mutation is a single G to A change in the splice donor consensus sequence at the 5' end of an intron located in the C-terminus intracellular domain. This mutation gives rise to two aberrantly spliced mRNAs detected by RT-PCR; a larger fragment resulting from failure to splice out the intron and a smaller fragment resulting from skipping of one exon. Both transcripts are predicted to shift the reading frame and produce abnormal proteins. Homozygous tg$^{la}$ mice, which have the splice mutation have more profound ataxia and cerebellar degeneration compared to the tg mice.

The findings that mutations in the $\alpha_{1A}$ Ca$^{2+}$ channel are associated with cerebellar ataxia and Purkinje and granule cell degeneration in the mouse support the hypothesis that this channel is critical for normal Purkinje and granule cell function in the cerebellum. The recessive nature of the two mutations in the mouse and the fact that the tg$^{la}$ mutation is predicted to generate an abnormal protein suggest that these mutations are causing the ataxia phenotype through a loss of function mechanism. The mutation in the tg$^{la}$ mice alter the carboxy terminus portion of the channel just up stream from the position of the putative glutamine tract in the human gene. These data raise interesting questions about the mechanism by which a modest glutamine expansion in the human $\alpha_{1A}$ Ca$^{2+}$ channel isoform leads to the cerebellar degeneration and ataxia. The dominant nature of the disease would suggest three possibilities: (1) loss of function due to haploinsufficiency, (2) a dominant negative effect due to the expansion, or (3) a novel gain of function as has been suggested in other diseases caused by CAG repeat expansions. The lack of ataxia phenotype in the tg and tg$^{la}$ mice heterozygous for the mutation would argue against the loss of function hypothesis. However, this model can not be ruled out until it is confirmed that either mutation in the mouse truly leads to a loss of the $\alpha_{1A}$ Ca$^{2+}$ channel function and that the heterozygous mice do not display ataxia nor Purkinje cell degeneration using careful quantitative measures. Given the transient and mild nature of the ataxia in some of the patients it could be extremely difficult to ascertain a mild and intermittent ataxia phenotype in the mice. A model invoking a dominant negative mechanism is compatible with the inheritance pattern in the human families and with data available sofar on the tg mice. In this model, the small expansion of the glutamine tract could interfere with the normal function of the channel either by affecting its binding to synaptic proteins or by hindering its association with other accessory channel proteins that are known to modulate its activity. Given that the $\alpha_{1A}$ $Ca^{2+}$ channel is now known to be important for normal Purkinje cell function based on electrophysiologic data[43] and the data in the tg mice, it is hard to argue that the glutamine expansion is conferring novel gain of function on the protein. The glutamine expansion most likely leads to aberrant channel function including the possibility of constitutive activation. The ultimate proof of the various models will await the generation of mice which lack the $\alpha_{1A}$ $Ca^{2+}$ channel gene and mice which express an allele with a CAG expansion in the SCA6 disease range.

The genotype/phenotype correlation in SCA6 suggests that the expansion is quite deleterious given the dramatic difference in the age of onset (28-31 years) in every member of the family carrying the 27 repeats as compared to the other families (40-50 years) when the repeat size is in the 22-23 repeat range. Although the sample size is too small at this time to draw firm conclusion about genotype/phenotype correlation, it would be interesting to see if some patients with HPCA/EA, which is much milder than SCA6, would have even smaller expansions. In addition, it would be important to determine if different mutations in the $\alpha_{1A}$ $Ca^{2+}$ channel lead to SCA6. The CAG repeat in SCA6 is stable without detectable mosaicism or intergenerational allele size changes. This is not surprising given that similar size CAG repeats at many other loci have been shown to be transmitted in a stable manner. However, the size of the repeat in the general population and the different sizes of expanded alleles in different SCA6 families suggest that some degree of instability does occur at this locus and that such instability has resulted in mutational expansions into the disease allele range.

In conclusion, the present invention demonstrates that a relatively small polyglutamine expansion in the human $\alpha_{1A}$ subunit of a Purkinje cell type $Ca^{2+}$ channel leads to Purkinje cell degeneration and cerebellar ataxia. The immediate implications of this finding are both clinical and biological. The observation that a relatively small CAG repeat expansion can lead to abnormal protein function provides a new concept about the effects of such repeats and the need to evaluate each carefully for possible pathogenic effects. Lastly, the expansion of a polyglutamine tract in a human calcium channel should provide insight about mechanisms of neurodegeneration as they pertain to calcium homeostasis and the possible role of such mechanisms in other glutamine-mediated neurodegenerative processes.

The following references were cited herein:
1. Warren, S. T. The expanding world of trinucleotide repeats. *Science* 271, 1374-1375 (1996).
2. The Huntington's disease collaborative research group. A novel gene containing a trinucleotide repeat that is expanded and unstable on Huntington's disease chromosomes. *Cell* 72, 971-983 (1993).
3. La Spada, A. R., Wilson, E. M., Lubahn, D. B., Harding, A. E. & Fischbeck, H. Androgen receptor gene mutations in X-linked spinal and bulbar muscular atrophy. *Nature* 352, 77-79 (1991).
4. Orr, H. et al. Expansion of an unstable trinucleotide (CAG) repeat in spinocerebellar ataxia type 1. *Nature Genet* 4, 221-226 (1993).
5. Pulst, S. M. et al. Moderate expansion of a normally biallelic trinucleotide repeat in spinocerebellar ataxia type 2. *Nature Genet.* 14, 269-276(1996).
6. Sanpei, K. et al. Identification of the gene for spinocerebellar ataxia type 2 using a direct identification of repeat expansion and cloning technique, DIRECT. *Nature Genet.* 14, 277-284 (1996).
7. Imbert, G., et al. Cloning of the gene for spinocerebellar ataxia 2 reveals a locus with high sensitivity to expanded CAG/glutamine repeats. *Nature Genet.* 14, 285-291 (1996).
8. Kawaguchi, Y. et al. CAG expansions in a novel gene for Machado-Joseph disease at chromosome 14q32.1. *Nature Genet* 8, 221-235 (1994).
9. Koide, R. et al. Unstable expansion of CAG repeat in hereditary dentatorubral-pallidoluysian atrophy (DRPLA). *Nature Genet* 6, 9-13 (1994).
10. Zoghbi, H. Y. & Caskey, C. T. Inherited disorders caused by trinucleotide repeat expansions. *Advances in Human Genetics*. Vol. (in press) (eds Harris, H. & Hirschorn, K. H.) (Plenum, N.Y., 1996).
11. Verkerk, A. J. M. H. et al. Identification of a gene (FMR-1) containing a CGG repeat coincident with a breakpoint cluster region exhibiting length variation in fragile X syndrome. *Cell* 65, 905-914 (1991).
12. Gu, Y., Shen, Y., Gibbs, R. A., and Nelson, D. L. Identification of FMR2, a novel gene associated with the FRAXE CCG repeat and CpG island. *Nature Genet* 13, 109-113 (1996).
13. Fu, Y.-H. et al. An unstable triplet repeat in a gene related to myotonic muscular dystrophy. *Science* 255, 1256-1259 (1992).
14. Campuzano, V. et al. Friedreich's ataxia: autosomal recessive disease caused by an intronic GAA triplet repeat expansion. *Science* 271, 1423-1427 (1996).
15. Chong, S. S., McCall, A. E., Cota, J., Subramony, S. H., Orr, H. T., Hughes, M. R., & Zoghbi, H. Y. Gametic and somatic tissue-specific heterogeneity of the expanded SCA1 CAG repeat in spinocerebellar ataxia type 1. *Nature Genet.* 10, 344-353 (1995).
16. Telenius, H. et al. Molecular analysis of juvenile Huntington disease: the major influence on (CAG)n repeat length is the sex of the affected parent. *Hum. Mol. Genet* 2, 1535-1540 (1993).
17. Housman, D. Gain of glutamines, gain of function. *Nature Genet* 10, 3-4, (1995).
18. Trottier, Y. et al. Polyglutamine expansion as a pathological epitope in Huntington's disease and four dominant cerebellar ataxias. *Nature* 378, 403-406 (1995).
19. Mori, Y. et al. Primary structure and functional expression from complementary DNA of a brain calcium channel. *Nature* 350, 398-402 (1991).
20. Starr, T. V. B., Prystay, W. & Snutch, T. P. Primary structure of a calcium channel that is highly expressed in the rat cerebellum. *Proc. Nat. Acad. Sci. USA* 88, 5621-5625 (1991).
21. Rettig, J., Sheng, Z-H., Kim, D. K., Hodson, C. D., Snutch, T. P., & Catterall, W. A. Isoform-specific interaction of the $\alpha_{1A}$ subunits of brain $Ca^{2+}$ channels with the presynaptic proteins syntaxin and SNAP-25. *Proc. Natl. Acad. Sci. USA* 93, 7363-7368 (1996).
22. Diriong, S., Williams, M. E., Ellis, S. B., Harpold, M. M. & Taviaux, S. Chromosomal localization of the human genes for $\alpha_{1A}$, $\alpha_{1B}$ and $\alpha_{1E}$ voltage-dependent $Ca^{2+}$ channel subunits. *Genomics* 30, 605-609 (1995).
23. Margolis et al, Characterization of cDNA clones containing CCA trinucleotide repeats derived from human brain. *Somat. Cell Mol. Genet* 21, 279-284 (1995)
24. Ophoff, R. A., et al. Familial hemiplegic migraine and episodic ataxia type 2 are cause by mutations in the $Ca^{2+}$ channel gene CACNL1A4. *Cell*, 87, 543-552 (1996).
25. Llinas, R., Sugimori, M., Hillman, D. E. & Cherksey, B. Distribution and functional significance of the P-type, voltage-dependent Ca²⁺ channels in the mammalian central nervous system. *Trends in Neurosci* 15, 351-355 (1992).
26. Cottingham, R. W., Idury, R. M., & Schaffer, A. A. Faster sequential genetic linkage computations. *Am. J. Hum. Genet* 53, 252-263 (1993).
27. Lathrop, G. M., Lalouel, J. M., Julier, C. & Ott, J. Strategies for multilocus linkage analysis in humans. *Proc. Natl. Acad. Sci. USA* 81, 3443-3446 (1984).
28. Subramony, S. H., Fratkin, J. D., Manyam, B. V. & Currier, R. D. Dominantly inherited cerebello-olivary atrophy is not due to a mutation at the spinocerebellar ataxia-I, Machado-Joseph disease, or Dentato-Rubro-Pallido-Luysian Atrophy locus. *Movement Disorders* 11:2, 174-180 (1996).
29. Stevanin, G. et al. A third locus for autosomal dominant cerebellar ataxia type 1 maps to chromosome 14q24.3-qter evidence for the existence of a fourth locus. *Am. J. Hum. Genet.* 54, 11-20 (1994).
30. Twells, R. et al. Autosomal dominant cerebellar ataxia with dementia: evidence of a fourth disease locus. *Hum. Mol. Genet.* 1, 177-190 (1994).
31. Vahedi, K. et al. A gene for hereditary paroxysmal cerebellar ataxia maps to chromosome 19 p. *Annals of Neurology* 37, 289-293 (1995).
32. Kramer, P. L. et al. A locus for the nystagmus-associated form of episodic ataxia maps to an 11-cM region on chromosome 19p. *Am. J. Hum. Genet.* 57, 182-185 (1995).
33. Joutel, A. et al. A gene for familial hemiplegic migraine maps to chromosome 19. *Nature Genet* 5, 41-45 (1993).
34. Elliott, M., Peroutka, S. J., Welch, S. & May, E. F. Familial hemiplegic migraine, nystagmus, and cerebellar atrophy. *Annals of Neurology* 39, 1, 100-106 (1996).
35. Koh, J. Y., & Cotman, C. W. Programmed cell death: its possible contribution to neurotoxicity mediated by calcium channel antagonist. *Brain Res.* 587, 233-240 (1996).
36. Catterall, W. A. Structure and function of voltage-gated ion channels. *Annu. Rev. Biochem.* 64, 493-531 (1995).
37. Perez-Reyes, E., Yuan, W., Wei, X., & Bers, M. Regulation of the cloned L-type cardiac calcium channel by cyclic-AMP-dependent protein kinase *FEBS Lett* 342, 119-123 (1994).
38. Stea, A., et al. Localization and functional properties of a rat brain $\alpha_{1A}$ calcium channel reflect similarities to neuronal Q-and P-type channels. *Proc. Natl. Acad. Sci. USA* 91, 10576-10580 (1994).
39. Birnbaumer, L., et al. The naming of voltage-gated calcium channels. *Neuron* 13, 505-506 (1994).
40. Zhang, J.-F.et al. Distinctive pharmacology and kinetics of cloned neuronal Ca²⁺ channels and their possible counterparts in mammalian CNS neurons. *Neuropharmacology* 32, 1075-1088 (1993).
41. Mintz, I. M., Adams, M. E., & Bean, B. P. P-type calcium channels in rat and peripheral neurons. *Neuron* 9, 85-95 (1992).
42. Fletcher, C. F. et al. Absence epilepsy in Tottering mutant mice is associated with calcium channel defects. *Cell* 87, 607-617 (1996).
43. Mintz, I. M. Block of Ca channels in rat central neurons by the spider toxin omega-Aga-IIIA. *J. Neurosci.* 14, 2844-2853 (1994).
44. Gubler, U., & Hoffman., B. J. A simple and very efficient method for generating cDNA libraries. *Gene* 25, 263-269 (1983).
45. Sambrook, J., Fritsch, E. F. & Maniatis, T. (1989) *Molecular Cloning. A Laboratory Manual.* (Cold Spring Harbor, N.Y., 1989).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of determining whether an individual has or is at risk for developing a spinocerebellar ataxia, wherein the method comprises analyzing a CAG repeat region of an alpha$_{1A}$ calcium channel subunit gene of said individual to detect a length polymorphism therein, wherein a length polymorphism of greater than 20 CAG repeat units indicates that said individual has or is at risk for developing a spinocerebellar ataxia.

2. The method of claim 1, wherein said analyzing the CAG repeat region comprises amplifying by polymerase chain reaction said CAG repeat region present in genomic DNA obtained from said individual using at least one oligonucleotide primer capable of amplifying said CAG repeat region, to produce an amplified CAG repeat region.

3. The method of claim 2, wherein said oligonucleotide primer is labeled.

4. The method of claim 3, wherein said oligonucleotide primer is fluorescently labeled.

5. The method of claim 4, wherein said fluorescent label is fluorescein, rhodamine, auramine, Texas Red, AMCA blue, or Lucifer yellow.

6. The method of claim 3, wherein said oligonucleotide primer is radiolabeled.

7. The method of claim 6, wherein said radiolabel comprises $^{32}$P.

8. The method of claim 3, wherein said oligonucleotide primer is labeled with an enzyme.

9. The method of claim 3, wherein said oligonucleotide primer is single stranded.

10. The method of claim 3, wherein said oligonucleotide primer is double stranded.

11. The method of claim 3, wherein said oligonucleotide primer comprises from between 15 to 25 nucleotides.

12. The method of claim 2, wherein said oligonucleotide primer comprises SEQ ID NO:1.

13. The method of claim 2, wherein said oligonucleotide primer comprises SEQ ID NO:2.

14. The method of claim 2, further comprising fractionating said amplified CAG repeat region by gel electrophoresis.

15. The method of claim 14, wherein the size of said amplified CAG repeat region is measured using said gel electrophoresis.

16. The method of claim 1, wherein said analyzing the CAG repeat region comprises measuring the size of the CAG repeat region.

17. The method of claim 1, wherein said analyzing comprises comparing the number of CAG nucleotide repeat units present in said CAG repeat region to a control sample.

18. The method of claim 17, wherein said control sample comprises a sequencing ladder.

19. The method of claim 17, wherein said control sample is from a subject who does not have SCA-6.

20. The method of claim 17, wherein said control sample comprises DNA or RNA from a subject who does not have SCA-6.

21. The method of claim 17, wherein said control sample was derived from a subject who does not have SCA-6.

22. The method of claim 1, wherein the method comprises obtaining a biological sample from said individual.

23. The method of claim 22, wherein the biological sample is a blood sample.

24. A method of determining whether an individual has or is at risk for developing a spinocerebellar ataxia, wherein the method comprises analyzing an allele of an alpha$_{1A}$ calcium channel subunit gene of said individual to detect a CAG repeat region length polymorphism therein, wherein a length polymorphism of greater than 20 CAG repeat units indicates that said individual has or is at risk for developing a spinocerebellar ataxia.

25. A method of detecting the presence or absence of a CAG trinuncleotide repeat expansion comprising analyzing a CAG repeat region of an alpha$_{1A}$ calcium channel subunit gene in a genomic DNA sample to detect a length polymorphism therein, wherein a number of CAG repeat units greater than 13 indicates the presence of a trinucleotide repeat expansion.

* * * * *

UNITED STATES PATENT AND TRADEMARK OFFICE
CERTIFICATE OF CORRECTION

PATENT NO. : 7,329,487 B2
APPLICATION NO. : 10/435804
DATED : February 12, 2008
INVENTOR(S) : Cheng-Chi Lee It is certified that error appears in the above-identified patent and that said Letters Patent is hereby corrected as shown below:

In claim 25, column 32, line 45, delete "trinuncleotide" and insert --trinucleotide-- therefor.

In claim 25, column 32, line 49, delete "13" and insert --20-- therefor.

Signed and Sealed this

Twenty-seventh Day of May, 2008

JON W. DUDAS
*Director of the United States Patent and Trademark Office*